(12) United States Patent
Gong et al.

(10) Patent No.: US 9,700,650 B2
(45) Date of Patent: *Jul. 11, 2017

(54) POLYSACCHARIDE BASED HYDROGELS

(75) Inventors: Glen Gong, San Carlos, CA (US); Suresh Subraya Pai, Mountain View, CA (US); Scott Robert Sershen, Foster City, CA (US)

(73) Assignee: SpotLight Technology Partners LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/505,683

(22) PCT Filed: Nov. 5, 2010

(86) PCT No.: PCT/US2010/055714
§ 371 (c)(1),
(2), (4) Date: Aug. 14, 2012

(87) PCT Pub. No.: WO2011/057131
PCT Pub. Date: May 12, 2011

(65) Prior Publication Data
US 2013/0045182 A1    Feb. 21, 2013

Related U.S. Application Data

(60) Provisional application No. 61/259,564, filed on Nov. 9, 2009.

(51) Int. Cl.
*A61K 47/36* (2006.01)
*A61L 26/00* (2006.01)
(Continued)

(52) U.S. Cl.
CPC .......... *A61L 26/0052* (2013.01); *A61K 47/10* (2013.01); *A61K 47/36* (2013.01);
(Continued)

(58) Field of Classification Search
CPC .. A61K 9/0024; A61K 9/5146; A61K 9/0014; A61K 9/2054; A61K 9/14;
(Continued)

(56) References Cited

U.S. PATENT DOCUMENTS 3,947,401 A    3/1976 Stamberger
4,016,106 A    4/1977 Sawyer et al.
(Continued)

FOREIGN PATENT DOCUMENTS

JP    2003-503367    1/2003
JP    2005-143920    6/2005
(Continued)

OTHER PUBLICATIONS

Chen et al., Biomaterials, 25:3725-3732, 2004.*
(Continued)

*Primary Examiner* — Jennifer McDonald
*Assistant Examiner* — Qing Xu
(74) *Attorney, Agent, or Firm* — Edward J. Baba; Khin K. Chin; Bozicevic, Field & Francis LLP

(57) ABSTRACT

Polysaccharide based hydrogel compositions and methods of making and using the same are provided. The subject polysaccharide based hydrogel compositions are prepared by combining a polysaccharide component with a hydrophilic polymer and a cross-linking agent. Also provided are kits and systems for use in preparing the subject compositions.

16 Claims, 9 Drawing Sheets

(51) Int. Cl.

| | |
|---|---|
| *A61K 47/10* | (2017.01) |
| *A61L 24/00* | (2006.01) |
| *A61L 24/04* | (2006.01) |
| *A61L 27/26* | (2006.01) |
| *A61L 27/34* | (2006.01) |
| *A61L 27/52* | (2006.01) |
| *A61L 31/04* | (2006.01) |
| *A61L 31/14* | (2006.01) |
| *C08J 3/075* | (2006.01) |
| *C08J 3/24* | (2006.01) |
| *A61K 47/48* | (2006.01) |

(52) U.S. Cl.
CPC ......... *A61L 24/0031* (2013.01); *A61L 24/043* (2013.01); *A61L 26/008* (2013.01); *A61L 27/26* (2013.01); *A61L 27/34* (2013.01); *A61L 27/52* (2013.01); *A61L 31/041* (2013.01); *A61L 31/145* (2013.01); *C08J 3/075* (2013.01); *C08J 3/246* (2013.01); *A61K 47/48784* (2013.01); *A61L 2400/04* (2013.01); *C08J 2300/105* (2013.01); *C08J 2371/02* (2013.01); *C08J 2400/106* (2013.01); *C08J 2405/08* (2013.01); *C08J 2471/02* (2013.01)

(58) Field of Classification Search
CPC .. A61K 9/0002; A61K 9/0012; A61K 9/5161; A61K 9/51; A61K 47/36–47/38; A61K 47/26; A61K 47/10; A61K 8/042; A61K 47/18
See application file for complete search history.

(56) References Cited

U.S. PATENT DOCUMENTS

| | | | |
|---|---|---|---|
| 4,134,871 A | 1/1979 | Otani et al. |
| 4,200,098 A | 4/1980 | Ayer et al. |
| 4,273,734 A | 6/1981 | Seiderman |
| 4,279,795 A | 7/1981 | Yamashita et al. |
| 4,285,987 A | 8/1981 | Ayer et al. |
| 4,359,558 A | 11/1982 | Gould et al. |
| 4,408,023 A | 10/1983 | Gould et al. |
| 4,434,153 A | 2/1984 | Urquhart et al. |
| 4,439,583 A | 3/1984 | Gould et al. |
| 4,439,584 A | 3/1984 | Gould et al. |
| 4,439,585 A | 3/1984 | Gould et al. |
| 4,485,089 A | 11/1984 | Leipold |
| 4,526,938 A | 7/1985 | Churchill et al. |
| 4,532,134 A | 7/1985 | Malette et al. |
| 4,542,176 A | 9/1985 | Graham |
| 4,549,952 A | 10/1985 | Columbus |
| 4,570,629 A | 2/1986 | Widra |
| 4,587,284 A | 5/1986 | Luissi et al. |
| 4,589,226 A | 5/1986 | Stensaas |
| 4,595,583 A | 6/1986 | Eckenhoff et al. |
| 4,632,826 A | 12/1986 | Ploger et al. |
| 4,642,233 A | 2/1987 | Urquhart et al. |
| 4,657,553 A | 4/1987 | Taylor |
| 4,663,149 A | 5/1987 | Eckenhoff et al. |
| 4,673,566 A | 6/1987 | Goosen et al. |
| 4,675,174 A | 6/1987 | Eckenhoff |
| 4,681,582 A | 7/1987 | Yamamoto |
| 4,683,092 A | 7/1987 | Tsang |
| 4,689,293 A | 8/1987 | Goosen et al. |
| 4,715,143 A | 12/1987 | Redenbaugh et al. |
| 4,731,384 A | 3/1988 | Dell et al. |
| 4,747,847 A | 5/1988 | Magruder et al. |
| 4,772,474 A | 9/1988 | Eckenhoff et al. |
| 4,781,714 A | 11/1988 | Eckenhoff et al. |
| 4,795,590 A | 1/1989 | Kent et al. |
| 4,802,997 A | 2/1989 | Fox et al. |
| 4,806,355 A | 2/1989 | Goosen et al. |
| 4,814,182 A | 3/1989 | Graham et al. |
| 4,836,928 A | 6/1989 | Aoyagi et al. |
| 4,842,867 A | 6/1989 | Ayer et al. |
| 4,844,984 A | 7/1989 | Eckenhoff et al. |
| 4,849,343 A | 7/1989 | Krull et al. |
| 4,865,552 A | 9/1989 | Maloney et al. |
| 4,875,287 A | 10/1989 | Creasy et al. |
| 4,889,664 A | 12/1989 | Kindt-Larsen |
| 4,900,552 A | 2/1990 | Sanvordeker et al. |
| 4,904,247 A | 2/1990 | Theirrrault et al. |
| 4,910,015 A | 3/1990 | Sung et al. |
| 4,925,677 A | 5/1990 | Feijen |
| 4,942,035 A | 7/1990 | Churchill et al. |
| 4,942,129 A | 7/1990 | Goosen et al. |
| 4,948,592 A | 8/1990 | Ayer et al. |
| 4,959,217 A | 9/1990 | Sanders et al. |
| 4,961,932 A | 10/1990 | Theeuwes |
| 4,983,385 A | 1/1991 | Hasegawa et al. |
| 4,986,987 A | 1/1991 | Ayer et al. |
| 4,990,582 A | 2/1991 | Salamone |
| 4,994,081 A | 2/1991 | Civerchia et al. |
| 5,000,957 A | 3/1991 | Eckenhoff et al. |
| 5,007,940 A | 4/1991 | Berg |
| 5,077,336 A | 12/1991 | Nakashita et al. |
| 5,089,606 A | 2/1992 | Cole et al. |
| 5,093,130 A | 3/1992 | Fujii et al. |
| 5,102,676 A | 4/1992 | Aldcroft et al. |
| 5,112,350 A | 5/1992 | Civerchia et al. |
| 5,112,618 A | 5/1992 | Cartmell et al. |
| 5,115,801 A | 5/1992 | Cartmell et al. |
| 5,116,387 A | 5/1992 | Berg |
| 5,120,344 A | 6/1992 | Libor |
| 5,120,544 A | 6/1992 | Henly |
| 5,134,057 A | 7/1992 | Kuypers et al. |
| 5,135,297 A | 8/1992 | Valint, Jr. |
| 5,143,646 A | 9/1992 | Nochumson et al. |
| 5,147,646 A | 9/1992 | Graham |
| 5,147,654 A | 9/1992 | Place et al. |
| 5,154,706 A | 10/1992 | Cartmell et al. |
| 5,160,328 A | 11/1992 | Cartmell et al. |
| 5,171,264 A | 12/1992 | Merrill |
| 5,172,514 A | 12/1992 | Weber et al. |
| 5,185,152 A | 2/1993 | Peyman |
| 5,186,936 A | 2/1993 | Groves |
| 5,192,326 A | 3/1993 | Bao et al. |
| 5,204,110 A | 4/1993 | Cartmell et al. |
| 5,212,622 A | 5/1993 | MacFarlane |
| 5,219,965 A | 6/1993 | Valint, Jr. |
| 5,232,724 A | 8/1993 | Aldcroft et al. |
| 5,242,828 A | 9/1993 | Bergstrom et al. |
| 5,264,214 A | 11/1993 | Rhee |
| 5,266,325 A | 11/1993 | Kuzma et al. |
| 5,277,915 A | 1/1994 | Provonchee et al. |
| 5,284,657 A | 2/1994 | Lu et al. |
| 5,288,497 A | 2/1994 | Stanley |
| 5,290,559 A | 3/1994 | Groves |
| 5,292,514 A | 3/1994 | Capecchi et al. |
| 5,292,515 A | 3/1994 | Moro et al. |
| 5,294,446 A | 3/1994 | Schlameus et al. |
| 5,304,595 A | 4/1994 | Rhee et al. |
| 5,306,500 A | 4/1994 | Rhee et al. |
| 5,306,504 A | 4/1994 | Lorenz |
| 5,314,420 A | 5/1994 | Smith |
| 5,322,935 A | 6/1994 | Smith |
| 5,324,775 A | 6/1994 | Rhee et al. |
| 5,328,955 A | 7/1994 | Rhee et al. |
| 5,331,059 A | 7/1994 | Engelhardt |
| 5,336,208 A | 8/1994 | Rosenbluth et al. |
| 5,336,501 A | 8/1994 | Czech et al. |
| 5,344,411 A | 9/1994 | Domb et al. |
| 5,348,973 A | 9/1994 | Raju et al. |
| 5,364,918 A | 11/1994 | Valint, Jr. et al. |
| 5,372,766 A | 12/1994 | Roe |
| 5,378,472 A | 1/1995 | Muzzarelli |
| 5,382,270 A | 1/1995 | Graham et al. |
| 5,385,543 A | 1/1995 | Haak et al. |
| 5,387,415 A | 2/1995 | Wunderlich et al. |
| 5,399,591 A | 3/1995 | Smith et al. |
| 5,406,945 A | 4/1995 | Riazzi et al. |
| 5,409,703 A | 4/1995 | McAnalley et al. |

(56) References Cited

U.S. PATENT DOCUMENTS

| | | |
|---|---|---|
| 5,423,736 A | 6/1995 | Cartmell et al. |
| 5,423,739 A | 6/1995 | Phipps et al. |
| 5,428,076 A | 6/1995 | Roe |
| 5,431,921 A | 7/1995 | Thombre |
| 5,436,066 A | 7/1995 | Chen |
| 5,436,161 A | 7/1995 | Bergstrom et al. |
| 5,443,955 A | 8/1995 | Cornell et al. |
| 5,447,499 A | 9/1995 | Allaire et al. |
| 5,447,727 A | 9/1995 | Graham |
| 5,451,406 A | 9/1995 | Lawin et al. |
| 5,464,629 A | 11/1995 | Monshipouri et al. |
| 5,464,932 A | 11/1995 | Allcock et al. |
| 5,468,505 A | 11/1995 | Hubbell et al. |
| 5,470,911 A | 11/1995 | Rhee et al. |
| 5,474,065 A | 12/1995 | Meathrel et al. |
| 5,482,719 A | 1/1996 | Guillet et al. |
| 5,483,697 A | 1/1996 | Fuchs |
| 5,490,984 A | 2/1996 | Freed |
| 5,492,840 A | 2/1996 | Malmqvist et al. |
| 5,510,418 A | 4/1996 | Rhee et al. |
| 5,512,299 A | 4/1996 | Place et al. |
| 5,512,492 A | 4/1996 | Herron et al. |
| 5,514,379 A | 5/1996 | Weissleder et al. |
| 5,516,532 A | 5/1996 | Atala et al. |
| 5,527,204 A | 6/1996 | Rhoades |
| 5,529,777 A | 6/1996 | Andrianov et al. |
| 5,531,716 A | 7/1996 | Luzio et al. |
| 5,531,999 A | 7/1996 | Cartmell et al. |
| 5,541,304 A | 7/1996 | Thompson |
| 5,543,441 A | 8/1996 | Rhee et al. |
| 5,575,815 A | 11/1996 | Slepian et al. |
| 5,578,307 A | 11/1996 | Wunderlich et al. |
| 5,597,560 A | 1/1997 | Bergamini et al. |
| 5,620,706 A | 4/1997 | Dumitriu et al. |
| 5,622,168 A | 4/1997 | Keusch et al. |
| 5,626,870 A | 5/1997 | Monshipouri et al. |
| 5,633,316 A | 5/1997 | Gartner et al. |
| 5,645,855 A | 7/1997 | Lorenz |
| 5,648,252 A | 7/1997 | Dumitriu et al. |
| 5,656,504 A | 8/1997 | Johansson et al. |
| 5,665,477 A | 9/1997 | Meathrel et al. |
| 5,667,778 A | 9/1997 | Atala |
| 5,677,196 A | 10/1997 | Herron et al. |
| 5,679,058 A | 10/1997 | Rhoades |
| 5,684,051 A | 11/1997 | Thompson |
| 5,684,058 A | 11/1997 | Nunez et al. |
| 5,684,059 A | 11/1997 | Salamone |
| 5,690,981 A | 11/1997 | Watanabe et al. |
| 5,698,213 A | 12/1997 | Jamiolkowski et al. |
| 5,700,289 A | 12/1997 | Breitbart et al. |
| 5,700,583 A | 12/1997 | Jamiolkowski et al. |
| 5,709,854 A | 1/1998 | Griffith-Cima et al. |
| 5,711,960 A | 1/1998 | Shikinami |
| 5,716,404 A | 2/1998 | Vacanti et al. |
| 5,718,862 A | 2/1998 | Thompson |
| 5,718,913 A | 2/1998 | Dhuique-Mayer et al. |
| 5,731,005 A | 3/1998 | Ottoboni et al. |
| 5,733,563 A | 3/1998 | Fortier |
| 5,736,313 A | 4/1998 | Spargo et al. |
| 5,747,570 A | 5/1998 | Date et al. |
| 5,750,585 A | 5/1998 | Park et al. |
| 5,752,974 A | 5/1998 | Rhee et al. |
| 5,762,620 A | 6/1998 | Cartmell et al. |
| 5,763,504 A | 6/1998 | Matsuda et al. |
| 5,766,908 A | 6/1998 | Klein et al. |
| 5,770,712 A | 6/1998 | Roy et al. |
| 5,785,993 A | 7/1998 | Baker et al. |
| 5,791,085 A | 8/1998 | Szmidt et al. |
| 5,792,471 A | 8/1998 | Curatolo |
| 5,792,617 A | 8/1998 | Rotman |
| 5,813,411 A | 9/1998 | Van Bladel et al. |
| 5,820,918 A | 10/1998 | Ronan et al. |
| 5,824,331 A | 10/1998 | Usala |
| 5,834,029 A | 11/1998 | Bellamkonda et al. |
| 5,837,789 A | 11/1998 | Stockhausen et al. |
| 5,838,863 A | 11/1998 | Fujiura et al. |
| 5,843,089 A | 12/1998 | Sahatjian et al. |
| 5,843,156 A | 12/1998 | Slepian et al. |
| 5,846,214 A | 12/1998 | Makuuchi et al. |
| 5,846,842 A | 12/1998 | Herron et al. |
| 5,851,229 A | 12/1998 | Lent et al. |
| 5,858,392 A | 1/1999 | Dumitriu et al. |
| 5,861,023 A | 1/1999 | Vachon |
| 5,869,172 A | 2/1999 | Caldwell |
| 5,874,500 A | 2/1999 | Rhee et al. |
| 5,879,713 A | 3/1999 | Roth et al. |
| 5,887,590 A | 3/1999 | Price |
| 5,888,540 A | 3/1999 | Sugden et al. |
| 5,891,477 A | 4/1999 | Lanza et al. |
| 5,897,874 A | 4/1999 | Stevens et al. |
| 5,900,245 A | 5/1999 | Sawhney et al. |
| 5,902,832 A | 5/1999 | Van Bladel et al. |
| 5,904,927 A | 5/1999 | Amiji |
| 5,906,934 A | 5/1999 | Grande et al. |
| 5,910,519 A | 6/1999 | Nunez et al. |
| 5,919,712 A | 7/1999 | Herron et al. |
| 5,922,352 A | 7/1999 | Chen et al. |
| 5,927,282 A | 7/1999 | Lenker et al. |
| 5,939,208 A | 8/1999 | Stoy |
| 5,942,209 A | 8/1999 | Leavitt et al. |
| 5,955,353 A | 9/1999 | Amiot |
| 5,955,729 A | 9/1999 | Nelson et al. |
| 5,964,644 A | 10/1999 | Rhoades |
| 5,968,556 A | 10/1999 | Atala et al. |
| 5,972,375 A | 10/1999 | Truter et al. |
| 5,973,014 A | 10/1999 | Funk et al. |
| 5,976,526 A | 11/1999 | Atala |
| 5,990,237 A | 11/1999 | Bently et al. |
| 5,994,440 A | 11/1999 | Staples et al. |
| 5,997,301 A | 12/1999 | Linden |
| 5,998,588 A | 12/1999 | Hoffman et al. |
| 6,007,833 A | 12/1999 | Chudzik et al. |
| 6,013,122 A | 1/2000 | Klitzman et al. |
| 6,017,301 A | 1/2000 | Schwartz |
| 6,018,388 A | 1/2000 | Nawacala |
| 6,027,721 A | 2/2000 | Hammang et al. |
| 6,027,744 A | 2/2000 | Vacanti et al. |
| 6,030,635 A | 2/2000 | Gertzman et al. |
| 6,044,201 A | 3/2000 | Van Turnhout |
| 6,045,835 A | 4/2000 | Soper et al. |
| 6,048,337 A | 4/2000 | Svedman |
| 6,051,248 A | 4/2000 | Sawhney et al. |
| 6,060,053 A | 5/2000 | Atala |
| 6,060,534 A | 5/2000 | Ronan et al. |
| 6,063,061 A | 5/2000 | Wallace et al. |
| 6,066,325 A | 5/2000 | Wallace et al. |
| 6,066,613 A | 5/2000 | Tsaur et al. |
| 6,074,660 A | 6/2000 | Jamiolkowski et al. |
| 6,080,412 A | 6/2000 | Jordan et al. |
| 6,087,450 A | 7/2000 | Breitbach et al. |
| 6,106,554 A | 8/2000 | Bretton |
| 6,106,875 A | 8/2000 | Soper et al. |
| 6,110,188 A | 8/2000 | Narciso, Jr. |
| 6,112,908 A | 9/2000 | Michaels |
| 6,113,629 A | 9/2000 | Ken |
| 6,120,807 A | 9/2000 | Gombotz et al. |
| 6,120,904 A | 9/2000 | Hostettler et al. |
| 6,124,273 A | 9/2000 | Drohan et al. |
| 6,126,616 A | 10/2000 | Sanyal |
| 6,129,761 A | 10/2000 | Hubbell |
| 6,132,765 A | 10/2000 | DiCosmo et al. |
| 6,136,873 A | 10/2000 | Hahnle et al. |
| 6,143,821 A | 11/2000 | Houben |
| 6,148,233 A | 11/2000 | Owen et al. |
| 6,153,222 A | 11/2000 | Becher |
| 6,156,572 A | 12/2000 | Bellamkonda et al. |
| 6,162,241 A | 12/2000 | Coury et al. |
| 6,164,012 A | 12/2000 | Lechelt-Kunze et al. |
| 6,171,610 B1 | 1/2001 | Vacanti et al. |
| 6,174,547 B1 | 1/2001 | Dong et al. |
| 6,180,132 B1 | 1/2001 | Huang et al. |
| 6,186,906 B1 | 2/2001 | Sullivan et al. |
| 6,190,603 B1 | 2/2001 | Steinmann et al. |
| 6,193,994 B1 | 2/2001 | Lee et al. |

(56) References Cited

U.S. PATENT DOCUMENTS

| | | |
|---|---|---|
| 6,200,600 B1 | 3/2001 | Rashid |
| 6,201,065 B1 | 3/2001 | Pathak et al. |
| 6,203,845 B1 | 3/2001 | Qin et al. |
| 6,210,712 B1 | 4/2001 | Edgran et al. |
| 6,214,369 B1 | 4/2001 | Grande et al. |
| 6,217,894 B1 | 4/2001 | Sawhney et al. |
| 6,221,238 B1 | 4/2001 | Grundig et al. |
| 6,224,893 B1 | 5/2001 | Langer et al. |
| 6,224,894 B1 | 5/2001 | Jamiolkowski et al. |
| 6,228,393 B1 | 5/2001 | DiCosmo et al. |
| 6,231,881 B1 | 5/2001 | Usala et al. |
| 6,238,403 B1 | 5/2001 | Greene, Jr. et al. |
| 6,245,357 B1 | 6/2001 | Edgran et al. |
| 6,251,823 B1 | 6/2001 | Yamaguchi et al. |
| 6,258,995 B1 | 7/2001 | Gilding et al. |
| 6,264,702 B1 | 7/2001 | Ory et al. |
| 6,268,161 B1 | 7/2001 | Han et al. |
| 6,271,278 B1 | 8/2001 | Park et al. |
| 6,271,345 B1 | 8/2001 | Waldmann et al. |
| 6,274,133 B1 | 8/2001 | Hu et al. |
| 6,274,175 B1 | 8/2001 | Gombotz et al. |
| 6,275,728 B1 | 8/2001 | Venkatraman et al. |
| 6,280,191 B1 | 8/2001 | Gordon |
| 6,281,015 B1 | 8/2001 | Mooney et al. |
| 6,281,319 B1 | 8/2001 | Mentak |
| 6,284,269 B1 | 9/2001 | Struengmann et al. |
| 6,287,588 B1 | 9/2001 | Shih et al. |
| 6,288,154 B1 | 9/2001 | Rhoades |
| 6,303,102 B1 | 10/2001 | Schlichte |
| 6,306,642 B1 | 10/2001 | Nelson et al. |
| 6,309,367 B1 | 10/2001 | Boock |
| 6,319,510 B1 | 11/2001 | Yates |
| 6,320,029 B1 | 11/2001 | Miekka et al. |
| 6,324,703 B1 | 12/2001 | Chen |
| 6,326,018 B1 | 12/2001 | Gertzman et al. |
| 6,333,194 B1 | 12/2001 | Levy et al. |
| 6,339,039 B1 | 1/2002 | Porath et al. |
| 6,340,598 B1 | 1/2002 | Herron et al. |
| 6,348,203 B1 | 2/2002 | Goodman et al. |
| 6,348,212 B2 | 2/2002 | Hymes et al. |
| 6,348,558 B1 | 2/2002 | Harris et al. |
| 6,350,463 B1 | 2/2002 | Herman et al. |
| 6,352,682 B2 | 3/2002 | Leavitt et al. |
| 6,360,129 B1 | 3/2002 | Ley et al. |
| 6,361,629 B2 | 3/2002 | Mahaffy |
| 6,361,790 B1 | 3/2002 | Rolf et al. |
| 6,361,797 B1 | 3/2002 | Kuzma et al. |
| 6,364,893 B1 | 4/2002 | Sahatjian et al. |
| 6,365,185 B1 | 4/2002 | Ritschel |
| 6,368,347 B1 | 4/2002 | Maini et al. |
| 6,372,248 B1 | 4/2002 | Qin et al. |
| 6,379,382 B1 | 4/2002 | Yang |
| 6,383,478 B1 | 5/2002 | Prokop et al. |
| 6,387,978 B2 | 5/2002 | Ronan et al. |
| 6,388,047 B1 | 5/2002 | Won et al. |
| 6,399,091 B1 | 6/2002 | Berthold et al. |
| 6,410,821 B1 | 6/2002 | Roe |
| 6,416,778 B1 | 7/2002 | Ragavan et al. |
| 6,423,332 B1 | 7/2002 | Huxel et al. |
| 6,428,576 B1 | 8/2002 | Haldimann |
| 6,432,449 B1 | 8/2002 | Goldenberg et al. |
| 6,436,441 B1 | 8/2002 | Sako et al. |
| 6,443,980 B1 | 9/2002 | Wang et al. |
| 6,444,217 B1 | 9/2002 | Kwok et al. |
| 6,444,324 B1 | 9/2002 | Yang et al. |
| 6,454,710 B1 | 9/2002 | Ballerstadt et al. |
| 6,455,065 B1 | 9/2002 | Hymes |
| 6,455,600 B1 | 9/2002 | Hahnle et al. |
| 6,458,375 B1 | 10/2002 | Gertzman et al. |
| 6,461,590 B2 | 10/2002 | Spears |
| 6,472,224 B1 | 10/2002 | Wischerhoff et al. |
| 6,475,516 B2 | 11/2002 | DiCosmo et al. |
| 6,475,750 B1 | 11/2002 | Han et al. |
| 6,488,952 B1 | 12/2002 | Kennedy et al. |
| 6,495,488 B2 | 12/2002 | Yamaguchi et al. |
| 6,506,408 B1 | 1/2003 | Palasis |
| 6,514,534 B1 | 2/2003 | Sawhney |
| 6,514,535 B2 | 2/2003 | Marchant |
| 6,514,689 B2 | 2/2003 | Han et al. |
| 6,517,866 B1 | 2/2003 | Am Ende et al. |
| 6,521,243 B2 | 2/2003 | Hassan |
| 6,521,431 B2 | 2/2003 | Kiser et al. |
| 6,524,327 B1 | 2/2003 | Spacek |
| 6,531,152 B1 | 3/2003 | Lerner et al. |
| 6,534,083 B2 | 3/2003 | Gilding et al. |
| 6,541,015 B2 | 4/2003 | Bentley et al. |
| 6,541,020 B1 | 4/2003 | Ding et al. |
| 6,544,287 B1 | 4/2003 | Johnson et al. |
| 6,544,543 B1 | 4/2003 | Mandrusov et al. |
| 6,544,544 B2 | 4/2003 | Hunter et al. |
| 6,544,548 B1 | 4/2003 | Siller-Jackson et al. |
| 6,552,103 B1 | 4/2003 | Bertozzi et al. |
| 6,554,813 B2 | 4/2003 | Kolby-Falk |
| 6,554,857 B1 | 4/2003 | Zilla et al. |
| 6,565,768 B1 | 5/2003 | Dentler et al. |
| 6,579,519 B2 | 6/2003 | Maitra |
| 6,579,978 B1 | 6/2003 | Renier et al. |
| 6,583,219 B2 | 6/2003 | Won et al. |
| 6,585,765 B1 | 7/2003 | Hossainy et al. |
| 6,586,493 B1 | 7/2003 | Massia et al. |
| 6,589,452 B2 | 7/2003 | Asher et al. |
| 6,589,549 B2 | 7/2003 | Shih et al. |
| 6,592,895 B2 | 7/2003 | Lang et al. |
| 6,596,296 B1 | 7/2003 | Nelson et al. |
| 6,596,402 B2 | 7/2003 | Soerens et al. |
| 6,596,763 B1 | 7/2003 | Thormar et al. |
| 6,602,294 B1 | 8/2003 | Sittinger et al. |
| 6,602,671 B1 | 8/2003 | Bawendi et al. |
| 6,602,952 B1 | 8/2003 | Bentley et al. |
| 6,602,975 B2 | 8/2003 | Hubbell et al. |
| 6,605,294 B2 | 8/2003 | Sawhney |
| 6,613,234 B2 | 9/2003 | Voute et al. |
| 6,630,457 B1 | 10/2003 | Aeschlimann et al. |
| 6,632,451 B2 | 10/2003 | Penhasi et al. |
| 6,632,457 B1 | 10/2003 | Sawhney |
| 6,642,363 B1 | 11/2003 | Mooney et al. |
| 6,649,187 B2 | 11/2003 | Hussain et al. |
| 6,652,874 B2 | 11/2003 | Ragavan et al. |
| 6,652,883 B2 | 11/2003 | Goupil et al. |
| 6,656,162 B2 | 12/2003 | Santini, Jr. et al. |
| 6,673,093 B1 | 1/2004 | Sawhney |
| 6,673,108 B2 | 1/2004 | Zilla et al. |
| 6,676,645 B1 | 1/2004 | Bitterhof |
| 6,676,971 B2 | 1/2004 | Goupil et al. |
| 6,681,521 B1 | 1/2004 | Holloway |
| RE38,431 E | 2/2004 | Miekka et al. |
| 6,685,697 B1 | 2/2004 | Arenberg et al. |
| 6,685,745 B2 | 2/2004 | Reever |
| 6,685,962 B2 | 2/2004 | Friedman et al. |
| 6,685,963 B1 | 2/2004 | Taupin et al. |
| 6,686,208 B2 | 2/2004 | Meusel et al. |
| 6,689,165 B2 | 2/2004 | Jacob et al. |
| 6,692,766 B1 | 2/2004 | Rubinstein et al. |
| 6,693,180 B2 | 2/2004 | Lee et al. |
| 6,696,496 B2 | 2/2004 | Oosterbaan et al. |
| 6,699,503 B1 | 3/2004 | Sako et al. |
| 6,699,504 B2 | 3/2004 | Rowe et al. |
| 6,702,983 B2 | 3/2004 | Hu et al. |
| 6,703,044 B1 | 3/2004 | Pinhassi et al. |
| 6,703,047 B2 | 3/2004 | Sawhney et al. |
| 6,706,279 B1 | 3/2004 | Hazzi |
| 6,706,690 B2 | 3/2004 | Reich et al. |
| 6,709,668 B2 | 3/2004 | Won et al. |
| 6,710,126 B1 | 3/2004 | Hirt et al. |
| 6,716,445 B2 | 4/2004 | Won et al. |
| 6,717,015 B2 | 4/2004 | Keltjens et al. |
| 6,723,304 B2 | 4/2004 | Stier |
| 6,723,344 B2 | 4/2004 | Sakiyama-Elbert et al. |
| RE38,522 E | 5/2004 | Gertzman et al. |
| 6,730,298 B2 | 5/2004 | Griffith-Cima et al. |
| 6,730,313 B2 | 5/2004 | Helmus et al. |
| 6,752,826 B2 | 6/2004 | Holloway et al. |
| 6,755,938 B2 | 6/2004 | Kehrer et al. |
| 6,761,895 B2 | 7/2004 | Sawada et al. |

(56) References Cited

U.S. PATENT DOCUMENTS

| | | |
|---|---|---|
| 6,770,721 B1 | 8/2004 | Kim |
| 6,773,703 B1 | 8/2004 | Ettner et al. |
| 6,773,713 B2 | 8/2004 | Bonassar et al. |
| 6,780,584 B1 | 8/2004 | Edman et al. |
| 6,783,838 B2 | 8/2004 | Coleman et al. |
| 6,793,789 B2 | 9/2004 | Choi et al. |
| 6,793,937 B2 | 9/2004 | Quong |
| 6,800,298 B1 | 10/2004 | Burdick et al. |
| 6,803,420 B2 | 10/2004 | Cleary et al. |
| 6,803,719 B1 | 10/2004 | Miller et al. |
| 6,805,836 B2 | 10/2004 | Salamone et al. |
| 6,808,938 B2 | 10/2004 | Hamalainen et al. |
| 6,818,018 B1 | 11/2004 | Sawhney |
| 6,821,331 B2 | 11/2004 | Damodaran |
| 6,824,535 B2 | 11/2004 | Kolby-Falk |
| 6,835,553 B2 | 12/2004 | Han et al. |
| 6,838,053 B2 | 1/2005 | John et al. |
| 6,846,291 B2 | 1/2005 | Smith et al. |
| 6,861,067 B2 | 3/2005 | McGhee et al. |
| 6,863,663 B1 | 3/2005 | Mills et al. |
| 6,867,245 B2 | 3/2005 | Iwata et al. |
| 6,881,420 B2 | 4/2005 | Flashner-Barak et al. |
| 6,884,428 B2 | 4/2005 | Binette et al. |
| 6,888,043 B2 | 5/2005 | Geiser et al. |
| 6,890,339 B2 | 5/2005 | Sahatjian et al. |
| 6,893,466 B2 | 5/2005 | Trieu |
| 6,896,874 B2 | 5/2005 | Li et al. |
| 6,897,072 B1 | 5/2005 | Rich et al. |
| 6,905,700 B2 | 6/2005 | Won et al. |
| 6,911,212 B2 | 6/2005 | Gertzman et al. |
| 6,911,216 B1 | 6/2005 | Roth et al. |
| 6,911,344 B1 | 6/2005 | Reichert et al. |
| 6,913,765 B2 | 7/2005 | Li et al. |
| 6,916,857 B2 | 7/2005 | Won et al. |
| 6,932,974 B2 | 8/2005 | Bezwada et al. |
| 6,939,568 B2 | 9/2005 | Burrell et al. |
| 6,940,580 B2 | 9/2005 | Winterton et al. |
| 6,946,443 B2 | 9/2005 | Blanchat et al. |
| 6,946,499 B2 | 9/2005 | Loomis et al. |
| 6,960,617 B2 | 11/2005 | Omidian et al. |
| 6,964,772 B1 | 11/2005 | Chornet et al. |
| 6,969,451 B2 | 11/2005 | Shin et al. |
| 6,991,652 B2 | 1/2006 | Burg |
| 6,991,804 B2 | 1/2006 | Helmus et al. |
| 6,991,848 B2 | 1/2006 | Thomson |
| 6,992,062 B2 | 1/2006 | Usala |
| 6,997,922 B2 | 2/2006 | Theeuwes et al. |
| 6,998,510 B2 | 2/2006 | Buckman et al. |
| 7,008,567 B2 | 3/2006 | Foulger et al. |
| 7,009,034 B2 | 3/2006 | Pathak et al. |
| 7,014,645 B2 | 3/2006 | Greene, Jr. et al. |
| 7,019,192 B2 | 3/2006 | Gertzman et al. |
| 7,022,343 B2 | 4/2006 | Philbrook et al. |
| 7,025,990 B2 | 4/2006 | Sawhney |
| 7,029,631 B2 | 4/2006 | Leonard et al. |
| 7,029,697 B2 | 4/2006 | Segura et al. |
| 7,032,251 B2 | 4/2006 | Janssen |
| 7,033,603 B2 | 4/2006 | Nelson et al. |
| 7,041,868 B2 | 5/2006 | Greene et al. |
| 7,045,141 B2 | 5/2006 | Merboth et al. |
| 7,045,366 B2 | 5/2006 | Huang et al. |
| 7,045,559 B2 | 5/2006 | Yahiahaoui et al. |
| 7,049,346 B1 | 5/2006 | Van Bladel et al. |
| 7,052,131 B2 | 5/2006 | McCabe et al. |
| 7,053,150 B2 | 5/2006 | Kozlowski et al. |
| 7,056,957 B2 | 6/2006 | Omidian et al. |
| 7,060,296 B2 | 6/2006 | Hennink et al. |
| 7,064,114 B2 | 6/2006 | Yiv et al. |
| 7,074,175 B2 | 7/2006 | Handy et al. |
| 7,083,806 B2 | 8/2006 | Rippon et al. |
| 7,084,099 B2 | 8/2006 | Radomyselski et al. |
| 7,091,283 B2 | 8/2006 | Muller et al. |
| 7,097,631 B2 | 8/2006 | Trautman et al. |
| 7,097,855 B1 | 8/2006 | Ameer et al. |
| 7,101,621 B2 | 9/2006 | Haddad et al. |
| 7,105,162 B1 | 9/2006 | Schmidt |
| 7,105,182 B2 | 9/2006 | Szymaitis |
| 7,105,352 B2 | 9/2006 | Asher et al. |
| 7,108,860 B2 | 9/2006 | Dueva et al. |
| 7,108,862 B2 | 9/2006 | Remington et al. |
| 7,108,865 B2 | 9/2006 | Curatolo et al. |
| 7,118,761 B2 | 10/2006 | Canada et al. |
| 7,128,929 B1 | 10/2006 | Scherr |
| 7,129,554 B2 | 10/2006 | Lieber et al. |
| 7,138,132 B2 | 11/2006 | Won et al. |
| 7,144,992 B2 | 12/2006 | Madhyastha |
| 7,147,867 B2 | 12/2006 | Dong et al. |
| 7,152,601 B2 | 12/2006 | Barakat et al. |
| 7,153,702 B2 | 12/2006 | Lin et al. |
| 7,156,877 B2 | 1/2007 | Lotz et al. |
| 7,157,428 B2 | 1/2007 | Kusanagi et al. |
| 7,163,920 B2 | 1/2007 | Dhanaraj et al. |
| 7,169,405 B2 | 1/2007 | Trieu |
| 7,172,866 B2 | 2/2007 | Hahn et al. |
| 7,175,430 B1 | 2/2007 | Gasser et al. |
| 7,175,895 B2 | 2/2007 | Janssen |
| 7,176,256 B2 * | 2/2007 | Rhee et al. .................. 525/54.1 |
| 7,182,783 B2 | 2/2007 | Trieu |
| 7,183,345 B2 | 2/2007 | Kim |
| 7,185,657 B1 | 3/2007 | Johnson et al. |
| 7,186,260 B2 | 3/2007 | Hyson |
| 7,189,414 B2 | 3/2007 | Rubinstein et al. |
| 7,195,778 B2 | 3/2007 | Fleshner-Barak et al. |
| RE39,587 E | 4/2007 | Gertzman et al. |
| 7,205,156 B2 | 4/2007 | Rich et al. |
| 7,211,060 B1 | 5/2007 | Talish et al. |
| 7,211,108 B2 | 5/2007 | Furst et al. |
| 7,217,294 B2 | 5/2007 | Kusanagi et al. |
| 7,217,520 B2 | 5/2007 | Tsinberg et al. |
| 7,220,491 B2 | 5/2007 | Rouns |
| 7,223,282 B1 | 5/2007 | Hossainy |
| 7,238,196 B2 | 7/2007 | Wibaux |
| 7,238,750 B2 | 7/2007 | Muller et al. |
| 7,247,314 B2 | 7/2007 | Hnojewyj et al. |
| 7,252,834 B2 | 8/2007 | Vyavahare et al. |
| 7,261,734 B2 | 8/2007 | Gellman et al. |
| 7,264,527 B2 | 9/2007 | Bawendi et al. |
| 7,267,958 B2 | 9/2007 | Dordick et al. |
| 7,276,246 B2 | 10/2007 | Zhang |
| 7,279,318 B1 | 10/2007 | Seymour et al. |
| 7,279,507 B2 | 10/2007 | Hu et al. |
| 7,303,575 B2 | 12/2007 | Ogle |
| 7,303,814 B2 | 12/2007 | Lamberti et al. |
| 7,309,232 B2 | 12/2007 | Rutherford et al. |
| 7,312,090 B2 | 12/2007 | Lin et al. |
| 7,314,636 B2 | 1/2008 | Caseres et al. |
| 7,320,962 B2 | 1/2008 | Reich et al. |
| 7,328,706 B2 | 2/2008 | Bardach et al. |
| 7,329,414 B2 | 2/2008 | Fisher et al. |
| 7,332,566 B2 | 2/2008 | Pathak et al. |
| 7,342,058 B2 | 3/2008 | Peppmoller et al. |
| 7,351,430 B2 | 4/2008 | St. John et al. |
| 7,364,675 B2 | 4/2008 | Guan et al. |
| 7,364,879 B2 | 4/2008 | Ho et al. |
| 7,371,257 B2 | 5/2008 | Sahatjian et al. |
| 7,371,258 B2 | 5/2008 | Woo et al. |
| 7,374,944 B2 | 5/2008 | Thompson et al. |
| 7,385,101 B2 | 6/2008 | Chandra et al. |
| 7,390,461 B2 | 6/2008 | Grier et al. |
| 7,393,259 B2 | 7/2008 | Heo et al. |
| 7,395,111 B2 | 7/2008 | Levin et al. |
| 7,407,646 B2 | 8/2008 | Laurent et al. |
| 7,407,912 B2 | 8/2008 | Mertens et al. |
| 7,410,651 B2 | 8/2008 | Villa et al. |
| 7,413,739 B2 | 8/2008 | Hubbell et al. |
| 7,413,752 B2 | 8/2008 | Sawhney |
| 7,414,039 B2 | 8/2008 | Parsons |
| 7,415,883 B2 | 8/2008 | Kaplan |
| 7,427,602 B1 | 9/2008 | Shea et al. |
| 7,429,378 B2 | 9/2008 | Serhan et al. |
| 7,431,152 B2 | 10/2008 | Marmo |
| 7,431,943 B1 | 10/2008 | Villa et al. |
| 7,432,069 B2 | 10/2008 | Barman et al. |
| 7,435,452 B2 | 10/2008 | Shimoyama et al. |

(56) References Cited

U.S. PATENT DOCUMENTS

| | | | |
|---|---|---|---|
| 7,452,868 B2 | 11/2008 | Kuzma et al. |
| 7,455,682 B2 | 11/2008 | Viola |
| 7,462,484 B2 | 12/2008 | Mizuno |
| 7,468,192 B2 | 12/2008 | Mizumo |
| 7,470,420 B2 | 12/2008 | Singaram et al. |
| 7,470,726 B1 | 12/2008 | Kross |
| 7,473,551 B2 | 1/2009 | Warthoe |
| 7,479,229 B2 | 1/2009 | Ho et al. |
| 7,503,936 B2 | 3/2009 | Trieu |
| 7,511,083 B2 | 3/2009 | Madsen et al. |
| 7,517,356 B2 | 4/2009 | Heinrich |
| 7,517,856 B2 | 4/2009 | Cohen et al. |
| 7,520,888 B2 | 4/2009 | Trieu |
| 7,520,900 B2 | 4/2009 | Trieu |
| 7,521,064 B2 | 4/2009 | Saxena et al. |
| 7,524,455 B2 | 4/2009 | Potyrailo |
| 7,524,514 B2 | 4/2009 | Brekke |
| 7,531,000 B2 | 5/2009 | Hodorek |
| 7,534,261 B2 | 5/2009 | Friedman |
| 7,547,447 B2 | 6/2009 | Yiu et al. |
| 7,553,903 B2 | 6/2009 | Riegel et al. |
| 7,560,432 B2 | 7/2009 | Kusanagi et al. |
| 7,569,222 B2 | 8/2009 | Woerly |
| 7,569,556 B2 | 8/2009 | Narayan et al. |
| 7,577,470 B2 | 8/2009 | Shah et al. |
| 7,578,846 B2 | 8/2009 | Trieu |
| 7,579,151 B2 | 8/2009 | Lee et al. |
| 7,584,630 B2 | 9/2009 | Van Gemert |
| 7,585,526 B2 | 9/2009 | Hamann |
| 7,592,418 B2 | 9/2009 | Pathak et al. |
| 7,600,378 B2 | 10/2009 | Yeghiazarian et al. |
| 7,605,232 B2 | 10/2009 | Pathak |
| 7,608,101 B2 | 10/2009 | Gellman et al. |
| 7,615,593 B2 | 11/2009 | Kao et al. |
| 7,618,461 B2 | 11/2009 | Trieu |
| 7,620,439 B2 | 11/2009 | Menon et al. |
| 7,622,459 B2 | 11/2009 | Gabrižová |
| 7,629,115 B2 | 12/2009 | Gu et al. |
| 7,629,172 B2 | 12/2009 | Alarcon et al. |
| 7,638,137 B2 | 12/2009 | Chauhan et al. |
| 7,642,240 B2 | 1/2010 | Cohen et al. |
| 7,648,713 B2 | 1/2010 | Sawhney |
| 2002/0193448 A1 | 12/2002 | Wallace et al. |
| 2006/0025815 A1 | 2/2006 | McGurk et al. |
| 2007/0031498 A1 | 2/2007 | Zong et al. |
| 2007/0275246 A1 | 11/2007 | Payne et al. |
| 2008/0069857 A1 | 3/2008 | Yeo |
| 2008/0187591 A1* | 8/2008 | Rhee .................... A61L 24/001 424/484 |
| 2009/0004276 A1* | 1/2009 | Ben-Shalom et al. ........ 424/488 |
| 2010/0291055 A1 | 11/2010 | Athanasiadis et al. |

FOREIGN PATENT DOCUMENTS

| | | |
|---|---|---|
| JP | 2006-524742 | 11/2006 |
| JP | 2008-505709 | 2/2008 |
| WO | 03/074099 | 9/2003 |

OTHER PUBLICATIONS

International Search Report for International Application No. PCT/US2010/055714, dated Mar. 21, 2011.
International Search Report for International Application No. PCT/US2010/055716, dated Mar. 21, 2011.
Choi et al. (2002) "Preparation of chitosan oligomers by irradiation" Polymer Degradation and Stability 78:533-538. (JP OA dtd Oct. 6, 2015).

* cited by examiner

POLYSACCHARIDE BASED HYDROGELS

CROSS-REFERENCE TO RELATED APPLICATIONS

This application claims the benefit of U.S. provisional Application No. 61/259,564, filed on Nov. 9, 2009, which is herein incorporated by reference in its entirety.

BACKGROUND OF THE INVENTION

Hydrogels are water-swollen networks of hydrophilic homopolymers or copolymers. These networks may be formed by various techniques; however, the most common synthetic route is the free radical polymerization of vinyl monomers in the presence of a difunctional cross-linking agent and a swelling agent. The resulting polymer exhibits both liquid-like properties, attributable to the major constituent, water, and solid-like properties due to the network formed by the cross-linking reaction. These solid-like properties take the form of a shear modulus that is evident upon deformation.

Hydrogels offer biocompatibility and have been shown to have reduced tendency for inducing thrombosis, encrustation and inflammation when used in medical devices. Unfortunately, the use of hydrogels in biomedical device applications has been hindered by poor mechanical performance. Many medical devices use hydrogels to improve device biocompatibility; however, many hydrogels can only be used in coatings as a result of insufficient mechanical performance for use as a bulk polymer. Many hydrogels suffer from low modulus, low yield stress, and low strength when compared to non-swollen polymer systems. Lower mechanical properties result from the swollen nature of hydrogels and the non-stress bearing nature of the swelling agent.

The state of the art hydrogel formulations do not adequately bind to all types of tissue surfaces. Furthermore, many of the existing hydrogel materials are not consistent in their ability to provide hemostatic control. The potency of these materials is limited by addressing one of the many qualities that are desirable in a hydrogel biomaterial (e.g. hemostasis or acting as an adhesion barrier, or providing infection control, or eliciting a minimal tissue response). A hydrogel biomaterial that addresses these multiple qualities consistently is not currently available in the art.

As such, there is a continuing need to develop new compositions capable of forming biocompatible hydrogel structures that offer improved therapeutic outcomes.

RELEVANT LITERATURE

U.S. Pat. Nos. 4,890,612; 4,963,489; 5,080,655; 5,192,302; 5,250,020; 5,266,480; 5,278,201; 5,278,204; 5,282,827; 5,324,775; 5,433,950; 5,599,916; 5,609,629; 5,618,622; 5,652,347; 5,690,955; 5,716,413; 5,725,498; 5,741,223; 5,827,937; 5,836,970; 5,852,024; 5,863,297; 5,874,417; 5,874,500; 5,888,988; 5,977,204; 6,001,352; 6,071,301; 6,156,068; 6,203,573; 6,323,278; 6,344,272; 6,350,244; 6,418,934; 6,428,811; 6,444,797; 6,511,511; 6,514,286; 6,530,994; 6,551,610; 6,566,406; 6,592,608; 6,602,952; 6,645,517; 6,783,712; 6,790,185; 6,890,343; 6,896,692; 6,994,712; 7,001,410; 7,083,635; 7,166,574; 7,226,615; 7,303,757; 7,329,414; 7,334,979; 7,335,220; 7,371,403; 7,414,028; 7,482,427; 7,482,503; 7,528,105; 7,670,592; 7,691,127; 7,766,891; and 7,776,022.

U.S. Pat. App. Nos. 2006/0241777, 2007/0196454, 2007/0231366, and 2009/0252781.

Foreign Patent Document No. WO 2009/028965.

Braunova et. al. Collect. Czech. Chem. Commun. 2004, 69: 1643-1656.

Carlson, R. P. et. al. Journal of Polymer Science, Polymer Edition. 2008, 19(8): 1035-1046.

SUMMARY OF THE INVENTION

Polysaccharide based hydrogel compositions and methods of making and using the same are provided. The subject polysaccharide based hydrogel compositions are prepared by combining a polysaccharide component with a hydrophilic polymer and a cross-linking agent. Also provided are kits and systems for use in preparing the subject compositions.

These and other objects, advantages, and features of the invention will become apparent to those persons skilled in the art upon reading the details of the disclosure as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
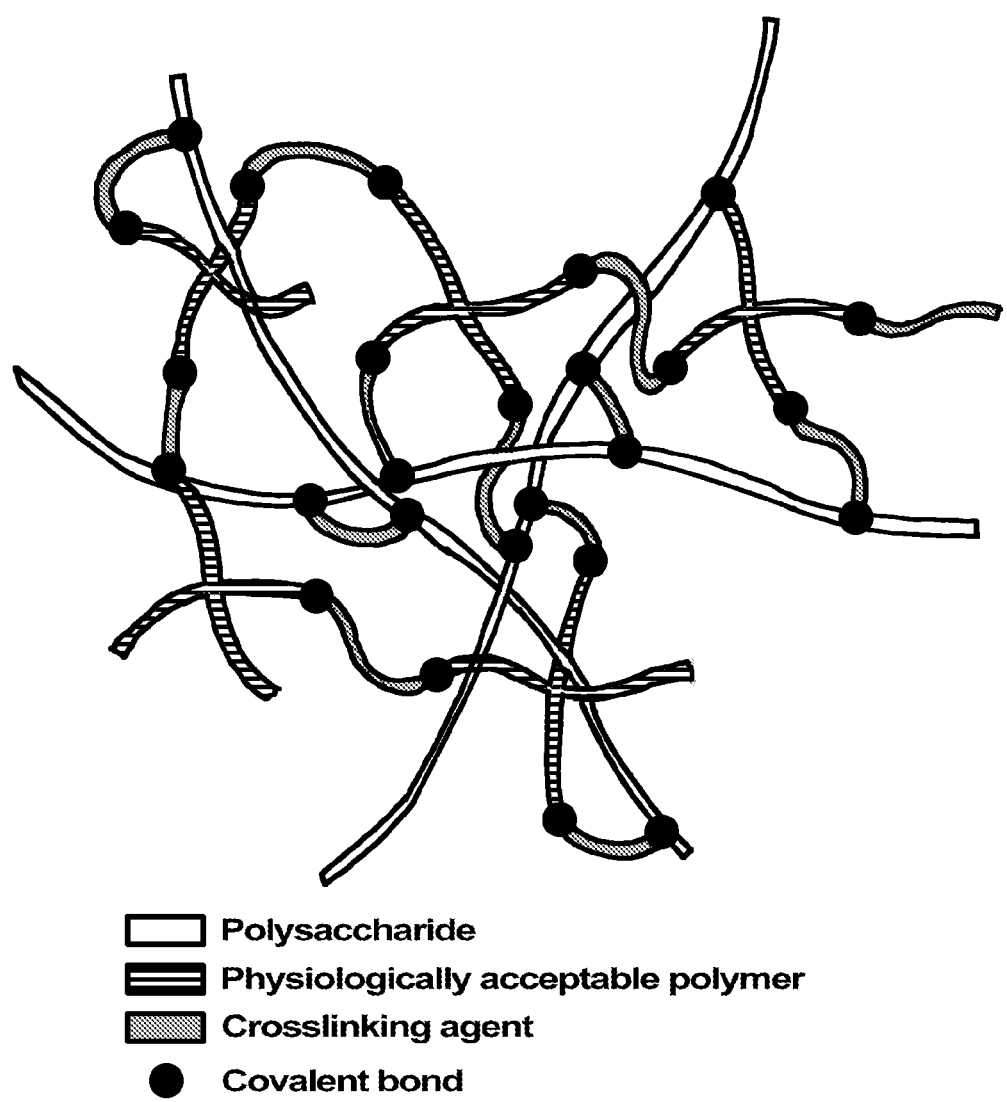
FIG. 1 shows a matrix of an exemplary polysaccharide based hydrogel.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the polymer" includes reference to one or more polymer and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

In general, the present invention includes hydrogel compositions that have been fabricated out of a polysaccharide and two or more additional components. The subject hydrogel compositions are characterized by being capable of bonding tissue in both wet (e.g., blood) and dry environments, where adhesion of the composition to the tissue is physiologically acceptable. A further feature of the subject compositions is that they are well tolerated and do not elicit a substantial inflammatory response, if any inflammatory response. The subject compositions can provide multiple desirable qualities such as a combination of any of the following: hemostatic properties, adhesive properties, re-vascularization, biocompatibility, bactericidal, bacteriostatic and/or fungicidal properties, tissue remodeling and/or provides a scaffold for tissue engineering, regeneration, and/or cell seeding, enzymatic or hydrolytic degradation pathways, swelling, engineered residence times, engineered viscosities, temperature or energy activation, inclusion of agents to enable visualization under imaging modalities (X-ray, CT, MRI, US, PET, CTA, etc.), engineered degree of hydrophilicity or hydrophobicity, gap and/or space filling, surface coating, ability to absorb energy, inclusion of foaming agents, inclusion of visual agents, ability to act as a drug delivery platform, media for sound transmission, and engineered durometer.

The subject polysaccharide based hydrogel compositions are prepared by combining or mixing a polysaccharide element and two ore more components, such as a polymer and a cross-linking agent. An exemplary matrix is provided in FIG. 1. Each of these precursor components or compositions is now reviewed separately in greater detail.

Compositions

As noted above, the compositions of the present invention include a polysaccharide component. Examples of polysaccharides suitable for use with the present invention include, but are not limited to, chitosan, hyaluronic acid, the family of chondroitin sulfates, heparin, keratan sulfate, glycogen, glucose, amylase, amylopectin and derivatives thereof. The polysaccharide may be naturally occurring or synthetically produced. Polysaccharides have several reactive groups that are available for chemical modification. These include the hydroxyl (OH), carboxyl (COOH), and acetamido ($COCH_3$) groups. Further functionality can be imparted to specific polysaccharides in the form of an amine ($NH_2$) group via basic deacetylation, in which a polysaccharide is exposed to basic conditions at elevated temperatures. The degree of deacetylation is dependent on the strength of the alkaline conditions, the temperature of the reaction environment, and the duration of the reaction. For example, the percentage of deacetylation can be controlled to obtain different chitosan molecules from a single source of chitin. Other methods of imparting functionality onto polysaccharides are known to the art, such as the functionalizing of native hyaluronic acid with amine groups through the use of a hydrazide as taught by Prestwich and Marecak in U.S. Pat. No. 5,874,417, which is herein incorporated by reference. In this method, the carboxyl group of the disaccharide is linked to a multi-functional hydrazide under acidic conditions in the presence of a soluble carbodiimide.

In certain embodiments, the polysaccharide is chitosan. Chitosan is a disaccharide formed through the deacetylation of chitin, a naturally occurring material found in crustacean shells and some fungi. Chitosan is a biocompatible, hydrophilic polymer with hemostatic and antimicrobial characteristics. The Chitosan may be from a natural occurring source or may be synthetically derived. Chitosan is described in detail is U.S. Pat. Nos. 5,836,970, 5,599,916, and 6,444,797, the disclosures of which are incorporated by reference herein in their entirety.

The non-polysaccharide components of the hydrogel material may include a hydrophilic polymer such as any of the following natural, synthetic, or hybrid polymers: poly(ethylene glycol), poly(ethylene oxide), poly(vinyl alcohol), poly(allyl alcohol), poly(vinylpyrrolidone), poly(alkylene oxides), poly(oxyethylated polyols), poly(ethyleneimine), poly(allylamine), poly(vinyl amine), poly(aminoacids), poly (ethyloxazoline), poly(ethylene oxide)-co-poly(propylene oxide) block copolymers, polysaccharides, carbohydrates, oligopeptides, and polypeptides. The polymer chains may include homo-, co-, or terpolymers of the above materials, in a linear or branched form, and derivatives thereof. These materials may crosslink into a hydrogel through the formation of covalent bonds through the action of chemically active groups that are present on the polysaccharide and the counterpart hydrophilic polymers. Among the chemically active groups that are preferred for use in the present invention are those that can form a covalent bond with the readily available nucleophilic or electrophilic residues.

Examples of electrophilic groups that can react with the nucleophilic groups present on component materials include but are not limited to carboxyl groups, isocyanates, thiocyanates, N-hydroxysuccinimide esters, glycidyl ethers, glycidyl epoxides, vinyl sulfones, maleimides, orthopyridyl disulfides, iodoacetamides, and carbodiimides. Examples of nucleophilic groups that can react with the electrophilic groups present on the component materials include but are not limited to anhydrides, primary, secondary, tertiary, or quaternary amines, amides, urethanes, ureas, hydrazides, sulfahydryl groups, or thiols. The preceding list of reactive groups serves as an illustrative example; extension to other nucleophilic and electrophilic moieties should be clear to those of skill in the art.

In one embodiment, the hydrogel composition is a three-component hydrogel that includes a multifunctional PEG with terminal nucleophilic groups, a multifunctional PEG with terminal electrophilic groups, and chitosan. When the polymeric components are reconstituted with the appropriate buffers and mixed, they react to form a cohesive hydrogel.

The multifunctional PEG with terminal nucleophilic groups may comprise a difunctionally activated, trifunctionally activated, tetrafunctionally activated, or a star-branched activated polymer. The molecular weight of the multifunctional nucleophilic PEG may be in the range of 1 kiloDalton (kD) to 100 kD; the range of 5 kD to 40 kD; or the range of 10 kD to 20 kD. The multifunctional nucleophilic PEG mass be present in mass percentages of at least 1%; at least 5%; at least 10%; at least 20%; at least 40%; at least 80%; at least 99%.

The multifunctional PEG with terminal electrophilic groups may comprise difunctionally activated, trifunctionally activated, tetrafunctionally activated, or a star-branched activated polymer. The molecular weight of the multifunctional electrophilic PEG may be in the range of 1 kD to 100 kD; the range of 5 kD to 40 kD; or the range of 10 kD to 20 kD. The multifunctional electrophilic PEG mass be present in mass percentages of at least 1%; at least 5%; at least 10%; at least 20%; at least 40%; at least 80%; at least 99%.

The polysaccharide (e.g., chitosan) may be present in a salt or amine form. The chitosan may have a molecular weight in the range of 10 Dalton to 1 kD; the range of 1 kD to 10 kD; the range of 10 kD to 100 kD; the range of 100 kD to 250 kD; the range of 250 kD to 500 kD; or the range of 500 kD to 1000 kD. The chitosan may have a degree of deacetylation in the range of 1% to 10%; the range of 10% to 20%; the range of 20% to 30%; the range of 30% to 40%; the range of 40% to 50%; the range of 50% to 60%; the range of 60% to 70%; the range of 70% to 80%; the range of 80% to 90%; or the range of 90% to 99%. The chitosan may be present in the set hydrogel in a mass percentage range of 0.01% to 0.1%; a range of 0.1% to 0.5%; a range of 0.5% to 1.0%; a range of 1.0% to 5%; a range of 5% to 10%; a range of 10% to 20%; a range of 20% to 40%; a range of 40% to 80%; or a range of 80% to 99%. In certain embodiments, the polysaccharide is chitosan. In further embodiments, the chitosan may also comprise a derivative of chitosan, such as N,O carboxymethylchitosan as described in U.S. Pat. No. 5,888,988 the disclosure of which is incorporated herein by reference in its entirety, or a dicarboxyl derivatized chitosan as described in WO 2009/028965 the disclosures of which are incorporated herein by reference in their entirety. For example, dicarboxyl derivatized chitosan may be crosslinked to a polyethylene glycol with at least two nucleophilic reactive groups via a polyethylene glycol with at least two electrophilic reactive groups.

Figure 2:
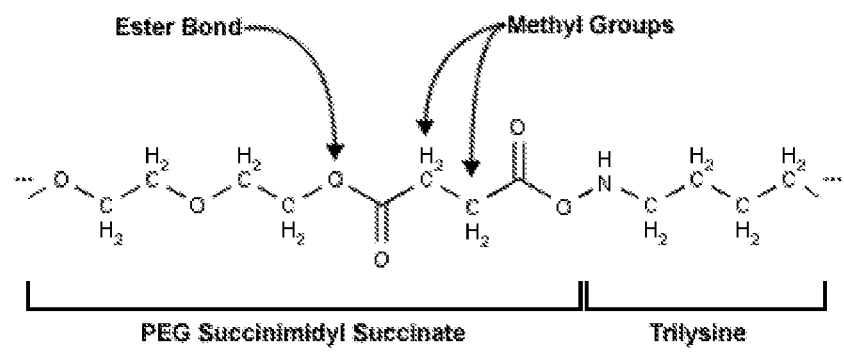
FIG. 2 shows the chemical structure for PEG Succinimidyl Succinate.

Hydrolytically degradable linkages may be incorporated into the backbone of the multifunctional PEG polymers. The inclusion of hydrolytically degradable chemical groups enables the resulting hydrogel to degrade after implantation in a controlled, consistent manner. The chemical groups that border the hydrolytically degradable linkages influence the rate of the hydrolysis reaction. Braunova et. al. (Collect. Czech. Chem. Commun. 2004, 69, 1643-1656) have shown that the rate of hydrolysis of ester bonds in poly(ethylene glycol) polymers decreases as the number of methylene groups that border the ester bond is increased. For example, a copolymer of trilysine and a multi-armed poly(ethylene glycol) succinimidyl succinate will degrade in approximately 8 days in aqueous media under physiological conditions. As shown in FIG. 2, the succinimidyl succinate has two methyl groups located next to the hydrolytically susceptible ester bond.

Figure 3:
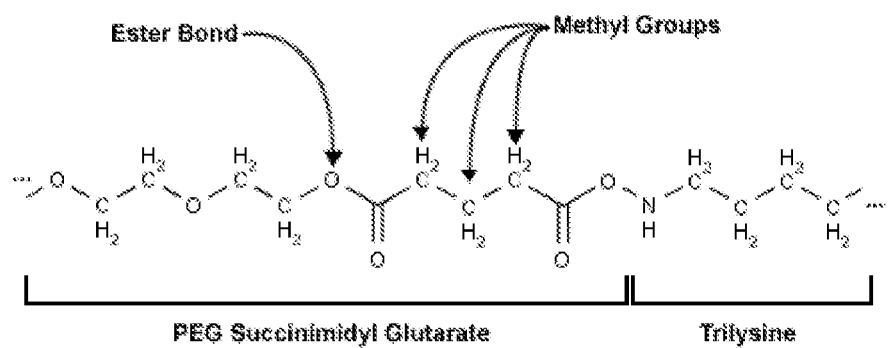
FIG. 3 shows the chemical structure for PEG Succinimidyl Glutarate.

By way of comparison, a copolymer of trilysine and a multi-armed poly(ethylene glycol) succinimidyl glutarate will degrade in approximately 50 days in aqueous media under physiological conditions. As shown in FIG. 3, the succinimidyl glutarate has three methyl groups located next to the hydrolytically susceptible ester bond.

As the number of methyl groups neighboring the ester bond increases, the rate of hydrolysis of the ester bond decreases. Further decreases in the rate of hydrolysis of the ester bond should be attained by increasing the number of methyl groups in the PEG polymer along the following progression: PEG succinimidyl adipate, PEG succinimidyl pimelate, PEG succinimidyl suberate, PEG succinimidyl azelate, PEG succinimidyl sebacate, etc. The extension of this method of controlling degradation times to other systems should be readily accessible to one of skill in the art.

Another form of the invention is a three-component hydrogel comprised of a multifunctional PEG with terminal nucleophilic groups, an aldehyde component, and chitosan. When the polymeric components are reconstituted with the appropriate buffers and mixed, they react to form a cohesive hydrogel.

The nucleophilic PEG and polysaccharide (e.g., chitosan) components in the composition are as described earlier. The aldehyde component in the composition as provided herein can be any biocompatible aldehyde with low toxicity. In particular, the aldehyde component includes a di-aldehyde, a polyaldehyde or a mixture thereof. The examples of the aldehyde include, but are not limited to, glyoxal, chondroitin sulfate aldehyde, succinaldehyde, glutaraldehyde, and male-aldehyde. In some embodiments, the aldehyde component is glutaraldehyde. Other suitable aldehydes which have low toxicity include multifunctional aldehydes derived from naturally-occurring substances, e.g., dextrandialdehyde, or saccharides. The aldehyde component can be an aldehyde product obtained by an oxidative cleavage of carbohydrates and their derivatives with periodate, ozone or the like. The aldehyde may optionally be pre-treated with heat. See U.S. Pat. No. 7,303,757 by Schankereli for "Biocompatible phase invertable proteinaceous compositions and methods for making and using the same". The aldehyde component can be analyzed for properties such as, viscosity, and osmolality. The aldehyde component of an adhesive composition can itself be further comprised of components and/or sub-components. Thus, the aldehyde component can be described in terms of weight, weight-to-weight, weight-to-volume, or volume-to-volume, either before or after mixing. For example, a polysaccharide may be crosslinked to a multi-functional synthetic polymer with at least two reactive nucleophilic groups via a dextran derivatized with aldehyde groups.

In some embodiments, the aldehyde component comprises of about 1-90% aldehyde concentration. In some embodiments, the aldehyde component comprises of about 1-75% aldehyde concentration. In some embodiments, the aldehyde component comprises of about 5-75% aldehyde concentration; about 10-75% aldehyde concentration; about 20-75% aldehyde concentration; about 30-75% aldehyde concentration; about 40-75% aldehyde concentration; about 50-75% aldehyde concentration; or about 60-75% aldehyde concentration.

The composition can comprise at least about 1% aldehyde concentration; at least about 5% aldehyde concentration; at least about 10% aldehyde concentration; at least about 20% aldehyde concentration; at least about 30% aldehyde concentration; at least about 40% aldehyde concentration; at least about 50% aldehyde concentration; at least about 60% aldehyde concentration; at least about 70% aldehyde concentration; at least about 80% aldehyde concentration; at least about 90% aldehyde concentration; or at least about 99% aldehyde concentration. In some embodiments, the adhesive composition comprises of about 1-30%, about 25-75%, about 50-75% or about 75-99% aldehyde concentration.

In some embodiments, the composition comprises of at least about 1% glutaraldehyde concentration; at least about 5% glutaraldehyde concentration; at least about 8% glutaraldehyde concentration; at least about 10% glutaraldehyde concentration; at least about 20% glutaraldehyde concentration; at least about 30% glutaraldehyde concentration; at least about 40% glutaraldehyde concentration; at least about 50% glutaraldehyde concentration; at least about 60% glutaraldehyde concentration; at least about 70% glutaraldehyde concentration; at least about 80% glutaraldehyde concentration; at least about 90% glutaraldehyde concentration; or at least about 99% glutaraldehyde concentration. In some embodiments, the composition comprises about 1-30%, about 25-75%, about 50-75% or about 75-99% glutaraldehyde concentration.

Thickening agents may be added to the forms of the invention described above. The thickening agents include, for example, dextran, carboxymethyl cellulose, polyethylene glycol, liposomes, proliposomes, glycerol, starch, carbohydrates, povidone, polyethylene oxide, and polyvinyl alcohol. In some embodiments, the thickening agent is dextran, polyethylene glycol or carboxymethyl cellulose. In some embodiments, the composition comprises at least about 1% thickening agent concentration; at least about 5% thickening agent concentration; at least about 10% thickening agent concentration; at least about 20% thickening agent concentration; at least about 30% thickening agent concentration; at least about 40% thickening agent concentration; at least about 50% thickening agent concentration; at least about 60% thickening agent concentration; at least about 70% thickening agent concentration; at least about 80% thickening agent concentration; or at least about 90% thickening agent concentration. In some embodiments, the composition comprises at least about 0.5%-10%, at least about 0.5%-25%, or at least about 0.5%-50% thickening agent concentration. In some embodiments, the thickening agent can comprise at least about 0.5% of the composition. The thickening agent can alter a gel time of the composition.

Some embodiments of the aforementioned aspects of the present invention may further comprise a radiopaque material. The radiopaque material includes, for example, bismuth oxide ($Bi_2O_3$), zinc oxide (ZnO), barium sulfate ($BaSO_4$) lanthanum oxide ($La_2O_3$), cerium oxide (CeO2), terbium oxide, ytterbium oxide, neodymium oxide, zirconia ($ZrO_2$), strontia (SrO), tin oxide ($SnO_2$), radiopaque glass and silicate glass. The radiopaque glass includes, for example, barium silicate, silico-alumino barium or strontium containing glass. The silicate glass includes, for example, barium or strontium containing glass. In some embodiments, the radiopaque material comprises at least about 0.001%; at least about 0.05%; at least about 0.1%; at least about 0.2%; at least about 0.5%; at least about 1%; at least about 2%; at least about 5%; at least about 8%; or at least about 10% of the adhesive composition.

The hydrogel compositions as provided herein can optionally contain a variety of naturally occurring or synthetically produced additives such as, but not limited to, water, buffer, saline solution, neutral salt, carbohydrate, fiber, miscellaneous biological material, wetting agent, antibiotics, preservative, dye, thickening agent, thinning agent, fibrinogen, polymer such as polyethylene glycol or combination thereof. Polymers include synthetic polymers such as, polyamides, polyesters, polystyrenes, polyacrylates, vinyl polymers (e.g., polyethylene, polytetrafluoro-ethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Polymers further include biological polymers which can be naturally occurring or produced in vitro by fermentation and the like. Biological polymers include, without limitation, collagen, elastin, silk, keratin, gelatin, polyamino acids, polysaccharides (e.g., cellulose and starch) and copolymers thereof.

Flexibilizers can be included in the hydrogel composition to provide flexibility to the material bond upon curing. Flexibilizers may be naturally occurring compositions or synthetically produced. Suitable flexiblizers include synthetic and natural rubbers, synthetic polymers, natural non-native biocompatible proteins (such as exogenous (i.e., non-native) collagen and the like), glycosaminoglycans (GAGs) (such as hyaluronin and chondroitin sulfate), and blood components (such as fibrin, fibrinogen, albumin and other blood factors).

The composition as provided herein can optionally include salts and/or buffers. Examples of the salt include, but are not limited to, sodium chloride, potassium chloride and the like. Suitable buffers can include, for example, ammonium, phosphate, borate, bicarbonate, carbonate, cacodylate, citrate, and other organic buffers such as tris(hydroxymethyl) aminomethane (TRIS), morpholine propanesulphonic acid (MOPS), and N-(2-hydroxyethyl) piperazine-N'(2-ethanesulfonic acid) (HEPES). Suitable buffers can be chosen based on the desired pH range for the hydrogel composition.

Additional additives may be present in the formulation to modify the mechanical properties of the composition. Some additives include, for example, fillers, softening agents and stabilizers. Examples of fillers include, but are not limited to, carbon black, metal oxides, silicates, acrylic resin powder, and various ceramic powders. Examples of softening agents include, but are not limited to, dibutyl phosphate, dioctylphosphate, tricresylphosphate, tributoxyethyl phosphates and other esters. Examples of stabilizers include, but are not limited to, trimethyldihydroquinone, phenyl-β-naphthyl amine, p-isopropoxydiphenylamine, diphenyl-p-phenylene diamine and the like.

One class of additives that may be included in the composition is nanoparticles or nanometer scale constructions. An example of nanoparticles that have been engineered to have specific physical characteristics are nanoshells, as taught by Oldenburg et. al. (U.S. Pat. No. 6,344,272, incorporated herein by reference in its entirety). Nanoshells are comprised of a metallic shell surrounding a non-conducting core; by varying the diameter of the core and the thickness of the shell, the absorption wavelength of the materials can be tuned to specific regions of the spectrum. West et. al. discloses the incorporation of nanoshells into a thermally sensitive polymer matrix for drug delivery in U.S. Pat. Nos. 6,428,811 and 6,645,517, and further teaches the use of nanoshells to treat tumors through localized hyperthermia in U.S. Pat. No. 6,530,994 (the above patents are herein incorporated by reference in their entirety). The combination of nanoparticles or other nanoscale structures with the composition of the invention may provide additional functionality (i.e. tunable absorption spectra) to the composition. In one example, the composition may be employed to fix the nanoparticles tuned to absorb near infrared light in a desired physical position prior to the application of a near-infrared laser to induce local hyperthermia. The incorporation of the nanoshells in the hydrogel matrix prevents the leaching of the nanoshells away from the target area.

The composition may also optionally include a plasticizing agent. The plasticizing agent provides a number of functions, including wetting of a surface, or alternately, increasing the elastic modulus of the material, or further still, aiding in the mixing and application of the material. Numerous plasticizing agents exist, including fatty acids, e.g., oleic acid, palmitic acid, etc., dioctylphtalate, phospholipids, and phosphatidic acid. Because plasticizers are typically water insoluble organic substances and are not readily miscible with water, it is sometimes advantageous to modify their miscibility with water, by pre-mixing the appropriate plasticizer with an alcohol to reduce the surface tension associated with the solution. To this end, any alcohol may be used. In one representative embodiment of this invention, oleic acid is mixed with ethanol to form a 50% (w/w) solution and this solution then is used to plasticize the polymer substrate during the formulation process. Whereas the type and concentration of the plasticizing agent is dependent upon the application, in certain embodiments the final concentration of the plasticizing agent is from about 0.01 to 10% (w/w), including from about 2 to about 4% (w/w). Other plasticizing agents of interest include, but are not limited to: polyethylene glycol, glycerin, butylhydroxytoluene, etc.

Fillers of interest include both reinforcing and non-reinforcing fillers. Reinforcing fillers may be included, such as chopped fibrous silk, polyester, PTFE, NYLON, carbon fibers, polypropylene, polyurethane, glass, etc. Fibers can be modified, e.g., as described above for the other components, as desired, e.g., to increase wettability, mixability, etc. Reinforcing fillers may be present from about 0 to 40%, such as from about 10 to about 30%. Non-reinforcing fillers may also be included, e.g., clay, mica, hydroxyapatite, calcium sulfate, bone chips, etc. Where desired, these fillers may also be modified, e.g., as described above. Non-reinforcing fillers may be present from about 0 to 40%, such as from about 10 to about 30%.

In certain embodiments, the composition may include a foaming agent which, upon combination with the crosslinker composition, results in a foaming composition, e.g., a composition that includes gaseous air bubbles interspersed about. Any convenient foaming agent may be present, where the foaming agent may be an agent that, upon contact with the crosslinking composition, produces a gas that provides bubble generation and, hence, the desired foaming characteristics of the composition. For example, a salt such as sodium bicarbonate in an amount ranging from about 2 to about 5% w/w may be present in the substrate. Upon combination of the substrate with an acidic crosslinker composition, e.g., having a pH of about 5, a foaming composition is produced.

Biologically active agents may be incorporated into the polymer network of the invention; these agents include but are not limited to naturally occurring or synthetically produced plasma proteins, hormones, enzymes, antibiotics, antiseptic agents, antineoplastic agents, antifungal agents, antiviral agents, anti-inflammatory agents, human and non human derived growth factors, anesthetics, steroids, cell suspensions, cytotoxins, cell proliferation inhibitors, and biomimetics The biologically active agents can be incorporated into the hydrogel of the invention by any means known in the art. As a non-limiting example, an agent or multiple agents may be added to the component solutions prior to mixing such that the hydrogel matrix forms around the agent or multiple agents and mechanically encapsulates the agent or agents. Alternatively, the agent or agents may be added to one or all of the component solutions prior to mixing. In another example, the agent or agents may be modified or derivatized to react with the components of the hydrogel and form covalent bonds with the hydrogel. The agent or agents may be bonded to the backbone of the hydrogel structure in a pendent chain configuration or as a fully integrated component of the hydrogel structure. In yet another example, the agent or agents may be suspended within a hydrophobic domain encapsulated within or distributed throughout the hydrogel. Alternatively, the agent or agents may be associated with the backbone of hydrogel through electrostatic, van Der Walls, or hydrophobic interactions. Combinations of any of the aforementioned techniques are also contemplated (e.g. a negatively charged agent that is physically encapsulated in a positively charged hydrogel matrix). The exact means of incorporation will be dictated by the nature of the biologically active agent.

Methods

Aqueous solutions of the component polymers are mixed to form the hydrogel of the invention. Generally, equal volumes of the aqueous component solutions are mixed to form the hydrogel. However, different ratios of the aqueous component solutions may be used provided the properties of the solutions are such that they crosslink to form the hydrogel of the invention when mixed. A person skilled in the art can achieve different curing times for the hydrogel of the invention by manipulating one or more of the following exemplary parameters:

a) the degree of deacetylation of the polysaccharide (e.g., chitosan);

b) the molecular weight of the polysaccharide (e.g., chitosan);

c) the species of the aldehyde component of the invention;
d) the mass percentage of the polymer components in the aqueous solutions;
e) the relative mass percentage of the respective polymer components in the aqueous solutions;
f) the molecular weight of the multifunctional nucleophilic PEG polymer;
g) the number of arms of the multifunctional nucleophilic PEG polymer;
h) the type of nucleophilic chemical groups resident on the multifunctional nucleophilic PEG polymer;
i) the molecular weight of the multifunctional electrophilic PEG polymer;
j) the number of arms of the multifunctional electrophilic PEG polymer;
k) the type of electrophilic chemical groups resident on the multifunctional electrophilic PEG polymer;
l) the concentration of buffer salts in the aqueous solutions;
m) the pH of the aqueous solutions; and
n) the viscosity of the aqueous solutions.

In one embodiment of the invention, the hydrogel is formed in situ. Aqueous solutions of the invention components can be simultaneously applied or deposited to a target area by spraying, streaming, injecting, painting or pouring of the solutions. The components mix upon application to or deposition at the target area and crosslink to form a polymer network. The formation of the polymer network in an aqueous media creates the hydrogel. Alternatively, the components may mix in transit to the target area. This may happen in the air in the case of the aerosolized or spray application, or in the lumen of a delivery device in the case of a streaming or injection delivery. The mixing of the component solutions may be aided by the use of static or active mixing elements in either delivery, such as inclusion of non-reactive elements to assist in mixing of the components, e.g., beads. Another method of application would be to mix the aqueous component solutions prior to delivery provided the cure time of the hydrogel was appropriately chosen.

The component solutions may be applied or deposited simultaneously to the target area, or in iterative fashion (application of an initial component solution followed by application of a second component solution, etc.). The method of application or deposition may be any described above, furthermore, the various methodologies and devices for performing in situ curing of a multi-component system may be used to apply the materials of the invention.

In another embodiment of the invention, the hydrogel is formed prior to application. The component solutions may be mixed in an appropriate vessel and allowed cure. The cured hydrogel may then be removed from the vessel and applied to the target area. Alternatively, the cured hydrogel may be dried prior to application to the target area. The term "drying" refers to any process by which the water content of a candidate polymer material is reduced from an initial value to a lower value. This may be accomplished by placing the material in an environment with lower water content than the polymer material under various temperature and pressure conditions, some of which are listed in Table 1.

TABLE 1

| Temperature | Pressure | Example |
| --- | --- | --- |
| Ambient | Ambient | Air drying |
| Elevated | Ambient | Oven drying |

TABLE 1-continued

| Temperature | Pressure | Example |
| --- | --- | --- |
| Ambient | Negative | Vacuum drying |
| Elevated | Negative | Vacuum oven drying |
| Reduced | Negative | Freeze drying |

Application of drying techniques beyond those listed herein should be readily accessible to one of skill in the art. For example, US. Published Pat. App. No. 2007/0231366 teaches a method of drying a hydrogel that comprises halting a solution of components undergoing crosslinking reaction prior to the completion of the reaction by reducing the temperature of the solution below the freezing point of the reacting solution, then subsequently freeze drying the partially-crosslinked hydrogel to remove the solvent from the partially crosslinked hydrogel. The partially crosslinked hydrogel is then processed through a series of treatments that serve to complete the crosslinking reaction. The reliance of this method of fabrication on a phase change between liquid and solid is cumbersome, and places limits on the production methods that can be employed in fabricated hydrogels by the taught method. For example, the timing of the transition of the solution from a liquid to solid state (i.e. freezing) is highly dependent on the physical and material characteristics of the mold (wall thickness, heat transfer coefficient, hydrophilicity or hydrophobicity of the mold surface), the freezing method (cold plate, freezer, immersion in liquid nitrogen, etc.), and the rate of the crosslinking reaction among others. Maintaining a consistent process in the face of these variables is challenging and can provide an obstacle to the scaled-up production of a hydrogel via the taught method.

One method for reducing the complexity of the process taught in US. Published Pat. App. No. 2007/0231366 is to use a method for halting or slowing the rate of the crosslinking reaction that is not subject to as many parameters as freezing, such as changing the pH of the solution of reacting components to a level that does not support further crosslinking For example, the reaction rate of a second-order nucleophilic substitution between an N-hydroxysuccinimide and a primary amine accelerates as the pH of the reaction media becomes more alkaline and decelerates as the pH of the reaction media becomes more acidic. Therefore, the addition of an aliquot of an acidic solution at a sufficient molarity and volume to shift the pH of the reacting media to an acidic condition will halt or slow the reaction rate of the nucleophilic substitution. Yet another means of changing the rate of reaction is by changing the ionic strength of the reaction media. The solution of hydrogel components is then ready for freeze drying. The benefit of this novel method is that the alteration of the reaction rate can be conducted while the hydrogel components are in the liquid phase (e.g. at room temperature), and is not dependent on the size, shape, or material of the casting mold. The independence of the method from the aforementioned limitations will improve consistency of batch-to-batch production lots by reducing the complexity and user-dependence of the process steps and lends itself to scale-up production by simplifying the use of larger molds.

The use of drying and other processing techniques (i.e. necking, stretching, machining, cutting, pressing, forming, etc.) can be combined to impart a shape memory characteristic to the formulation. As an example, a mold of the composition may be cast in the shape of a cylindrical tube and subsequently air dried until the moisture content of the material has reached equilibrium with environment (as determined by mass or other appropriate methods). The dried formulation may then be subjected to a necking process in which the dry hydrogel is heated and stretched to reduce the diameter and increase the length of the cylinder. When cooled to room temperature, the cylinder retains its necked dimensions. Upon absorbing water, the cylinder reverts to its cast length and dimension. The preceding example demonstrates one method of manipulating the formulation to attain a shape memory feature in response to hydration; the extension of this concept to other external stimuli (i.e. pH, ultrasound, radiation, temperature, etc.) should be accessible to one of skill in the art.

In one embodiment of the invention, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker The solutions may be mixed as part of the delivery system for use as an in situ crosslinking material via spray or liquid application, or the solutions may be cast into a mold after mixing to produce a hydrogel for subsequent application without further modification, or the resultant hydrogel may be dried and processed as described previously.

In a second embodiment, the polysaccharide and synthetic polymer are dissolved in a neutral or basic buffer along with a visible dye molecule such as methylene blue, blue dextran, FD&C Blue No. 1, FD&C Blue No. 2, FD&C Green No. 3, FD&C Red No. 40, FD&C Red No. 3, FD&C Yellow No. 5, FD&C Yellow No. 6, among others. The crosslinker is dissolved in an appropriately buffered solution. The solutions are mixed as described above in the prior embodiments to form the hydrogel. The inclusion of the dye material allows the user to ascertain the thickness and/or location of the hydrogel at the site of application. As an example, the dye may be used to infer the thickness of a coating of the hydrogel applied via a spray or aerosol to a tissue surface by observing changes in the intensity of the dye color as the thickness of the coating increases. As another example, the dye may be used to confirm the coverage of a mold or casting form as a step in a manufacturing process. Alternatively, the visible dye is present in solution with the crosslinker As yet another alternative, one or more dyes may be included in the polysaccharide/synthetic polymer solution and the crosslinker solution. For example, a blue dye may be added to the polysaccharide/synthetic polymer solution and a yellow dye may be added to the crosslinker solution to allow visual confirmation of mixing of the two components, as the combined solutions will have a green color when well mixed. Permutations of these techniques with different dyes, combinations of dyes, inclusion of dyes in one or both of the polysaccharide/synthetic polymer solutions, and the like to will be clear to one of skill in the art.

In a third embodiment, a radio-opaque material may be included with the polysaccharide and synthetic polymer in a neutral or basic buffer. Alternatively, the radio-opaque material may be included with the buffered crosslinker solution, or the radio-opaque material may be included in both the polysaccharide/synthetic polymer solution and the crosslinker solution. The solutions are mixed as described above in the prior embodiments to form a hydrogel that comprises a radio-opaque element dispersed within the body of the hydrogel. The presence of the radio-opaque element allows the visualization of the hydrogel via fluoroscopy when a direct line of sight (i.e. direct visualization) to the hydrogel is not available. For example, an in-situ crosslinking embodiment of the invention may be delivered to a patient through a standard cardiovascular catheter as an embolic agent for the occlusion of uterine fibroids. The location of the hydrogel may be observed as a dark or opaque mass on the output of a fluoroscopic imaging system.

In a fourth embodiment, a thickening agent may be added to either the neutral to basic solution of polysaccharide and synthetic polymer, the buffered crosslinker solution, or both solutions. The two solutions are combined to initiate the crosslinking reaction and form the hydrogel as described for prior embodiments. The thickening agent may be chosen such that it does not comprise chemical groups that will react with any or all of the polysaccharide, synthetic polymer, or crosslinker components. Alternatively, the thickening agent may be monofunctional, in that it comprises a single reactive group that can bind to a complementary chemical group on any or all of the polysaccharide, synthetic polymer or crosslinker components. The presence of the thickening agent serves to increase the viscosity of one or both of the polysaccharide/synthetic polymer and crosslinker solutions. As an example, a thickening agent may be added to the crosslinker solution if the polysaccharide/synthetic polymer solution is significantly more viscous than the crosslinking solution prior to the addition of the thickening agent. Matching the viscosity of the two component solutions can improve the mixing of the solutions to produce a more consistent, homogenous hydrogel structure and reduce variability that may be present in the rate of the crosslinking reaction due to incomplete or inefficient mixing among other improvements in handling. As another example, a thickening agent may be added to either or both of the polysaccharide/synthetic polymer and crosslinker solutions to produce a solution that resists migration from the point of delivery prior to complete crosslinking and formation of the hydrogel. In an exemplary case of the delivery of an in-situ crosslinking embodiment of the hydrogel, a highly viscous material will not be washed away, diffused, or otherwise diluted during the time between delivery and completion of the crosslinking reaction.

In a fifth embodiment, a steroid may be combined with a crosslinker in a neutral to acidic buffer. The polysaccharide and synthetic polymer are dissolved in a neutral to basic buffer solution. The two solutions are combined to initiate the crosslinking reaction and form the hydrogel as described for prior embodiments, entrapping the steroid in the hydrogel network. Steroids are generally insoluble in basic or alkaline solutions, therefore the addition of a steroid to the neutral to acidic buffer containing the crosslinker acts to prevent or mitigate the precipitation of the steroid out of solution prior the incorporation of the steroid into the hydrogel. Upon application to a wound, or implantation into a subject, the steroid will either diffuse out of the hydrogel at a rate dictated in part by the pore size of the hydrogel, or it will remain entrapped in the hydrogel until the hydrogel degrades to a point that allows for diffusion of the steroid into the surrounding anatomy.

In a sixth embodiment, an antibiotic such as gentamicin may be combined with a crosslinker in a neutral to acidic buffer. The polysaccharide and synthetic polymer are dissolved in a neutral to basic buffer solution. The two solutions are combined to initiate the crosslinking reaction and form the hydrogel as described for prior embodiments, entrapping the steroid in the hydrogel network. Antibiotics are generally insoluble in basic or alkaline solutions, therefore the addition of an antibiotic to the neutral to acidic buffer containing the crosslinker acts to prevent or mitigate the precipitation of the antibiotic out of solution prior the incorporation of the steroid into the hydrogel. Upon application to a wound, or implantation into a subject, the antibiotic will either diffuse out of the hydrogel at a rate dictated in part by the pore size of the hydrogel, or it will remain entrapped in the hydrogel until the hydrogel degrades to a point that allows for diffusion of the antibiotic into the surrounding anatomy.

In a seventh embodiment, a fully crosslinked form of the composition of the invention may be used as a carrier for platelet-rich-plasma (PRP). The fully crosslinked form of the hydrogel is submerged into a solution of PRP in a state of less than equilibrium swelling to absorb the PRP into the interstices of the hydrogel network. The fully crosslinked state of the hydrogel may include but is not limited to forms such as an air dried form, a fully cured but not yet dried (semi-hydrated) form, a lyophilized form, and a dried and fragmented form among others. The PRP-loaded composition of the invention is then applied to a target anatomy, such as a soft tissue defect (e.g. tendon, ligament, hernia, rotator cuff, etc.), a laceration or external wound bed (e.g. pressure sore, diabetic ulcer, etc.), or a hard tissue defect (e.g. bone) to deliver the PRP to the target area over a specified period of time. Alternatively, an external material may be used to absorb and carry the PRP (e.g. gauze sponge, TephaFLEX® knitted monofilament mesh, TephaFLEX® absorbable film, collagen sponge, bandages, other scaffold materials, etc.) with the composition of the invention applied to the surface of the carrier to form a hydrogel coating and act as a barrier to diffusion of the PRP out of the carrier material. Calcium, thrombin or collagen may optionally be added to activate the release of growth factors from the PRP. The method of application may include but is not limited to a spray application, dip-coating, and painting among others.

It should be clear that the examples of incorporating the steroid, antibiotic, and PRP into the composition of the invention can be extended to any biologically active agent, including but not limited to naturally occurring or synthetically produced plasma proteins, hormones, enzymes, antiseptic agents, antineoplastic agents, antifungal agents, antiviral agents, anti-inflammatory agents, human and non human derived growth factors, anesthetics, cell suspensions, cytotoxins, cell proliferation inhibitors, fibrin, fibrinogen, collagen, and biomimetics.

In an eighth embodiment, a fiber such as methylcellulose may be added to the composition to prevent adsorption of the material across the gastrointestinal track. Methylcellulose may be added to a solution of fragmented hydrogel in an appropriate buffer for this purpose.

In a ninth embodiment, a wetting agent such as oleic acid may be added to either the neutral to basic solution of polysaccharide and synthetic polymer, the buffered crosslinker solution, or both solutions. The two solutions are combined to initiate the crosslinking reaction and form the hydrogel as described for prior embodiments. The wetting agent serves to promote curing and adhesion of an in-situ composition of the hydrogel onto an oily target surface such as the skin, liver or gall bladder.

In a tenth embodiment, a flexibilizer such as collagen may be added to either the neutral to basic solution of polysaccharide and synthetic polymer, the buffered crosslinker solution, or both solutions. The two solutions are combined to initiate the crosslinking reaction and form the hydrogel as described for prior embodiments. The type and quantity of flexibilizer incorporated into the hydrogel composition can be adjusted to vary the ductility and elasticity of the cured hydrogel.

In an eleventh embodiment, specific salts and/or buffers can be used as solvents for dissolving the polysaccharide, synthetic polymer, and crosslinker. For example, the polysaccharide and synthetic polymer may be dissolved in a sodium borate buffer adjusted to a neutral or basic pH. The crosslinker may be dissolved in a sodium phosphate buffer adjusted to a neutral or acidic pH. The combination of the two solutions will result in a buffered solution containing the three components of the hydrogel at a pH that results in a crosslinking reaction rate that is appropriate for a given application (e.g. gelation in less than 10 seconds for a spray application, gelation in less than 10 minutes for a casting application, etc.). Specific salts and buffers may be chosen to accommodate additional components that may comprise the composition of the invention. For example, monosodium phosphate salt may be used to achieve an acidic buffer suitable for dissolving both the crosslinker and a steroid.

In a twelfth embodiment, a filler such as hydroxyapatite, fibrous silk, carbon fiber, bone chips, a mesh of polyglycolic acid, a mesh of TephaFLEX® and the like may be added to either the neutral to basic solution of polysaccharide and synthetic polymer, the buffered crosslinker solution, or both solutions. The two solutions are combined to initiate the crosslinking reaction and form the hydrogel as described for prior embodiments. The filler serves to alter the mechanical characteristics of the hydrogel, including but not limited to strength, toughness, tear resistance, compressive modulus, and tensile modulus. Alternatively, the polysaccharide and synthetic polymer are dissolved in a neutral or basic buffer. The crosslinker is dissolved in an appropriately pH balanced buffer. The two solutions are combined and poured or sprayed into a mold containing the filler material to allow the formation of a hydrogel network between the polysaccharide, the synthetic polymer, and the crosslinker around and/or within the filler.

In a thirteenth embodiment, a stabilizer such as trimethyldihydroquinone may be added to either the neutral to basic solution of polysaccharide and synthetic polymer, or a powder form of the crosslinker component. The inclusion of a stabilizer serves to extend the shelf life of the components prior to mixing in the in-situ crosslinking configurations of the invention. At the point of use, the powder form of the crosslinker is dissolved in an appropriately pH balanced buffer solution and combined with the polysaccharide/synthetic polymer solution to initiate the crosslinking reaction and form the hydrogel as described for prior embodiments.

In a fourteenth embodiment, a foaming agent such as sodium bicarbonate may be added to either the neutral to basic solution of polysaccharide and synthetic polymer, the buffered crosslinker solution, or both solutions. The two solutions are combined to initiate the crosslinking reaction and form the hydrogel as described for prior embodiments. The presence of the sodium bicarbonate induces the formation of bubbles and the foaming of the mixture of reacting solutions, resulting in a hydrogel that exhibits a macroporous structure. Alternatively, the foaming agent can be added to a mixture of the polysaccharide/synthetic polymer and crosslinker solutions after the two solutions have been mixed (while the crosslinking reaction is progressing). In another method, the foaming agent can be placed in a mold or cast that receives the combined polysaccharide/synthetic polymer and crosslinker solutions. The average pore size, distribution of pore sizes, total pore volume and other characteristics of the foamed hydrogel can be controlled by adjusting the amount of foaming agent incorporated into the composition of the invention.

In a fifteenth embodiment, an absorbent sponge is fabricated by freeze drying the product of the combination of a neutral to basic buffer comprising the polysaccharide and synthetic polymer and an appropriately pH balanced buffer comprising the crosslinker. The sponge may be swelled in a solution comprising a biologically or pharmaceutically active agent, and then coated with a in-situ crosslinking formulation of the composition of the invention. The release of the biologically or pharmaceutically active agent would be dependent on the size of the agent relative to the mesh size of the in-situ cured coating. If the size of the agent is significantly higher than the mesh size of the coating, the agent would be retained until the coating has substantially degraded or worn away. If the size of the agent is approximately similar to the mesh size of the coating, the agent would diffuse out of the sponge at a rate dictated in part but not limited to the diffusion gradient across the coating, the tortuosity of the average path through the coating, the charge of the agent relative to the coating, the thickness of the coating, and the degree of hydration of the coating, among other parameters. The coating may be applied using a spraying and/or dip coating method, as an overmolded casting technique, or other methods known in the art. The coating may integrate into the surface of the sponge through covalent bonding, mechanical interlocking, or charge differences among others. Alternatively, the coating may not integrate with the sponge and serve as free-floating shell or frictionally bound shell around a core the sponge material. The coating may be applied to the core sponge when the sponge is in the hydrated, semi-hydrated, or dried states. For example, the core sponge may be coated in the dry state, and the coated sponge may be immersed in a loading solution of biologically or pharmaceutically active agent. Alternatively, the core sponge may be immersed in a loading solution of biologically or pharmaceutically active agent, allowed to dry, then coated in the dry state. In another example, the core sponge may be immersed in an appropriate solution to a desired level of hydration and coated, with the resultant hydrated core, coated material immersed in a second solution containing a biologically or pharmaceutically active agent. Any of the above examples may be implanted in the dry, semi-hydrated, or hydrated states after loading of the coated sponge is substantially complete.

In another example, a biologically or pharmaceutically active agent may be incorporated into the polysaccharide and synthetic polymer solution and/or the crosslinker solution during the fabrication of the core sponge material. The incorporation may comprise but is not limited to covalent bonding, electrostatic and/or van Der Walls interactions, hydrophobic interactions, and entrapment among others. The loaded sponge material may then be coated with an in-situ crosslinked coating as described above. The in-situ crosslinked coating may comprise at least one additional, different, biologically or pharmaceutically active agent to enable the delivery of at least two different agents from a single material. The release rates of the agents would be dictated by their respective diffusion constants through the core sponge and/or the coating and the degradation rates of the core sponge and/or coating. In another example, the same biologically or pharmaceutically active agent may be loaded into the sponge and the core to achieve an extended or modulated release profile. The release profile can be modified by altering the degradation times of the sponge and coatings, the density of the hydrogel network of the sponge and coatings, the relative size of the sponge and the thickness of the coatings among others. In yet another example, one agent may be incorporated into the sponge during the fabrication of the sponge, a second agent may be loaded into the sponge through a swelling method as previously described, and a third may be incorporated into the coating. Additionally, layering successive coats of in-situ curing polymer can be performed to modify the structural, mechanical, and release profiles of the materials. Each layer may have unique properties including but not limited to degradation times, method of degradation, crosslink density, percentage of polymeric material, equilibrium swelling, ductility, compressive modulus, hydrophilicity, and the like. It should be obvious to one of skill in the art that permutations of the structural and mechanical characteristics of the coating and sponge, the order of loading of the materials with active agents, and the type of active agents beyond those listed here are achievable.

In a sixteenth embodiment, the polysaccharide and synthetic polymer are dissolved in a neutral or basic buffer. The crosslinker is dissolved in an appropriately pH balanced buffer. The two solutions are combined to allow the formation of a hydrogel network between the polysaccharide, the synthetic polymer, and the crosslinker with a gelation time on the order of tens of minutes. The combined solutions are transferred into a mold wherein the volume of the solution is less than the volume of the mold. The mold is then rotated (e.g. using a lathe, centrifuge, or similar apparatus) to coat the internal walls of the mold with the combined solution. The rotation of the mold is halted after gelation is complete, and the hollow, cured hydrogel is removed from the mold. The hollow hydrogel may be dried at this point by any of the method described earlier. The cavity in the center of the hydrogel can be used as a reservoir for a biologically or pharmaceutically active agent, a saline solution, or the like. The cavity may be filled with a desired solution prior to or after implantation of the hydrogel into the target anatomy. The cavity may be refilled with the desired solution via a syringe, catheter, filling tube, or other mechanism if the solution elutes out of the material prior to the conclusion of a course of treatment.

Utility

The compositions described herein may combine multiple utilities as described below. For example, the hydrogel may be applied or deposited to prevent leakage across suture lines or anastomoses following therapeutic or interventional procedures, including coronary artery bypass grafting, carotid endarterectomy, synthetic graft procedures as described in U.S. Pat. No. 7,303,757, biopsy as described in U.S. Pat. Nos. 6,350,244, 6,592,608, 6,790,185, 6,994,712, 7,001,410, 7,329,414, and 7,766,891, liver or kidney transplantation as described in U.S. Pat. No. 7,226,615, hernia repair, gastric bypass, lung resection, lung volume reduction, bone void filling, cartilage repair as described in U.S. Pat. Nos. 5,716,413, 5,863,297, 5,977,204, 6,001,352, 6,156,068, 6,203,573, 6,511,511, 6,514,286, and 6,783,712, and topical incisions as described in U.S. Pat. Nos. 7,371, 403, 7,482,503, and 7,776,022 (acting as a hydrogel bandage), wounds, or ulcers. All recited patents listed in the preceding paragraph are herein incorporated by reference in their entirety.

In ophthalmology, the sealant may be used to seal clear corneal incisions to provide a soft lubricious surface barrier to protect the ocular surface incisions from the external environment, such as described in U.S. Published Pat. App. Nos. 2007/0196454 and 2009/0252781. In neurosurgery and/or orthopedic surgery, the sealant may be used to repair dural tears or incisions to ensure a water tight seal preventing CSF leakage as taught in U.S. Pat. No. 6,566,406. All recited patents listed in the preceding paragraph are herein incorporated by reference in their entirety.

The composition may be used as an embolic for aneurysmal closure. The form of the invention may include but is not limited to the following: a liquid composition that crosslinks to form a solid material in the aneurysm, a dry composition that swells when exposed to liquid within the aneurysm, and a dry coating placed over a traditional coil to improve the efficacy and space filling characteristics of the coil. The composition may be used for the occlusion of neurovascular and/or peripheral aneurysm or the occlusion of Fallopian tubes and/or seminal vesicles for sterilization. Additional applications of the composition on the invention are in varicose vein embolization, uterine fibroid embolization, embolization of hypervascularized tumors, embolization of arterio-venous malformations, meningioma embolization, paraganglioma tumor embolization, and metastatic tumor embolization as taught in U.S. Pat. No. 7,670,592 and herein incorporated herein by reference in its entirety. The treatment of tumors may or may not include chemotherapeutic agents as a component of the hydrogel.

The composition may be used as a hemostat. One form of the invention is a solid bandage for hemorrhagic control in trauma in civilian and military applications as a first responder survival means as described in U.S. Pat. Nos. 7,371,403, 7,482,503, and 7,776,022. A further example of the use of the composition of the invention as a hemostat is to close punctures of the femoral radial or brachial arteries post catheter based diagnostic or interventional procedures as taught in U.S. Pat. Nos. 7,331,979, 7,335,220, 7,691,127, 6,890,343, 6,896,692, 7,083,635, 4,890,612, 5,282,827, 5,192,302, and 6,323,278. An additional example is the management of traumatized, broken, burned, or lacerated mucosal linings, such as the tonsils post tonsillectomy, adenoids post adenoidectomy, after tooth removal, to treat dental dry socket, to treat epistaxis, or treat disruption of any other mucosal surfaces where bleeding control is required. The composition may be used to provide hemostatic control post removal of tissue for biopsy purposes as experienced in liver, lung, kidney, breast, soft tissue, and lymph node biopsies as taught in U.S. Pat. Nos. 5,080,655, 5,741,223, 5,725,498, and 6,071,301. All recited patents listed in the preceding paragraph are herein incorporated herein by reference in their entirety.

The composition may be used to act as an agent for the treatment of diabetic foot ulcers, venous stasis ulcers, pressure ulcers, or ulcers and lacerations of any type that require advanced wound management. The purpose of these materials is to provide a moist environment to cover and protect the exposed tissue, and sometimes to stimulate optimal healing as taught in U.S. Pat. Nos. 4,963,489, 5,266,480, and 5,443,950. All patents listed in the preceding paragraph are herein incorporated herein by reference in their entirety.

The composition may be used as an adhesion barrier in general, gynecologic, and ENT surgical applications to reduce the incidence, extent, and severity of post-operative adhesions. Adhesions are a type of scar tissue that forms a connection between two organs or surfaces that are normally separate in the body. It is hypothesized that the free blood and plasma that result from surgery can form fibrin strands between tissues acutely; these strands can mature within a time span of days into permanent tissue bands which can interfere with normal organ function and lead to other serious clinical complications. They are sometimes associated with endometriosis and pelvic inflammatory disease and are known to frequently form after abdominal, pelvic, or sinus surgery as taught in U.S. Pat. Nos. 5,852,024, 6,551, 610, and 5,652,347. Over 90% of patients that undergo surgical procedures of this type may form adhesions. The composition may be formed such that a lumen is maintained in the body of the composition to enable ongoing airflow (i.e. during application following sinus surgery) or drainage of fluids. The composition may also be used as a stent to maintain separation between tissues. For example, the composition may be formed into a cylindrical structure and inserted into a sinus ostium that has been dilated to maintain the dilation of the ostium while the tissue heals. In another example, the composition may be used as an ethmoid spacer to maintain an opening into the ethmoid sinuses following surgery. In yet another example, the composition of the invention may be a cylindrical structure of freeze-dried hydrogel that is immersed in a solution of a biologically or pharmaceutically active agent, coated with an in-situ crosslinkable composition of the invention, and inserted into the frontal or ethmoid cells to provide local delivery of the biologically or pharmaceutically active agent. All patents listed in the preceding paragraph are herein incorporated herein by reference in their entirety.

The compositions described herein may be used as a surface coating on medical devices or tissues to prevent the formation of biofilm, and bacterial or fungal colonies. The selection of a strongly cationic polysaccharide (e.g., Chitosan) as a component of the hydrogel network allows for a continuous surface coating on implants and disposable medical devices that provides a hindrance to biofilm deposition (Carlson, R. P. et. al., Anti-biofilm properties of chitosan coated surfaces. Journal of Polymer Science, Polymer Edition, 19(8): pp 1035-1046, 2008). The mechanism of action may be twofold, the physical structure of the polysaccharide may function disrupt the bacterial cell wall or the cationic nature of the polysaccharide may be exploited to bind with anionic antibiotic agents. Alternatively, a non-polysaccharide component or additive may be used to provide similar antimicrobial, antibacterial, or antifungal properties (e.g. silver). An important application of a surface coated that provides infection control is in the prevention or treatment of osteomyelitis. Osteomyelitis is an infection of bone or bone marrow with a propensity for progression due to pyrogenic bacteria. The presentation of osteomyelitis can be observed due to iatrogenic causes such as joint replacements, internal fixation of fractures, or root canalled teeth. The hydrogel composition of this invention could allow for localized sustained antibiotic therapy. Furthermore, the composition may be designed to prevent or mitigate bacterial or fungal infections, reducing or eliminating the need for prolonged systemic antibiotic therapy as taught in U.S. Pat. Nos. 5,250,020, 5,618,622, 5,609,629, and 5,690,955. All patents listed in the preceding paragraph are herein incorporated herein by reference in their entirety.

The compositions described herein can be used effectively to form porous and non-porous scaffolds of controlled microstructure favorable to cell seeding and tissue engineering applications. Methods of control of pore size and structure include the following: freeze drying (lyophilization), salt extraction, the use of foaming agents such hydrogen peroxide, and other methods well known in the art. Multiple cell lines are of contemporary interest to enable the growth and repair of complex tissues using these porous and non-porous scaffolds such as vasculature, epithelial tissue, Islet cells for the formation of a tissue engineered pancreas, nerve regeneration, cartilage regeneration and repair, bone growth and repair, and connective and soft tissue repair (ventral and inguinal hernia, pelvic floor reconstruction, vaginal slings, rotator cuffs, tendon, etc.).

The hydrogel composition of this invention may used in the controlled delivery or administration of therapeutic or palliative agents. The composition may include a synthetic component that acts as a carrier or depot for the therapeutic or palliative agent. The agent may be covalently bound to the structure of the hydrogel matrix or physically entrapped within the hydrogel matrix. The rate of release of the therapeutic or palliative agents may be controlled by modifying the composition of the invention. In one example, the composition may be formed into a hollow chamber to allow injection of a solution containing therapeutic or palliative agents. The chamber containing the therapeutic or palliative agents is then placed at the target anatomy (e.g. inserted into the ethmoid sinus, the frontal sinus cells, agar nasi cells, maxillary sinus, etc.) and the agent or agents then diffuse through the wall of the chamber over time. Alternatively, the therapeutic or palliative agent may be incorporated into the structure of the composition via bonding or encapsulation. This allows the release profile of the therapeutic or palliative agents to be modified by either the diffusion rate of the agent or agents through the hydrogel or the degradation rate of the hydrogel, or both mechanisms proceeding concurrently. In another example, the hollow chamber may be inserted into the target anatomy, then filled with a solution containing the therapeutic or palliative agents of interest. Targets of contemporary interest include the following: paclitaxel for the treatment of tumors, insulin for the treatment of diabetes, analgesics or anesthetics for the treatment of pain, vasoconstrictors for the control of blood pressure such as amphetamines, antihistamines, pseudo-ephedrine, and caffeine, vasodilators for the control of blood pressure such as alpha blockers, nitric oxide inducers, and papavarine, cholesterol lowering drugs such as statins (e.g., lovostatin), procoagulants for the control of clotting such as protamine sulfate, thrombin, fibrin, and collagen, anticoagulants for the control of clotting such as heparin, coumadin, glycoprotein 2-β-3-α, warfarin, abciximab, Ticagrelor, and clopidogrel bisulfate, and selective serotonin reuptake inhibitors such as fluoxetine to provide palliative treatment of depression, obsessive/compulsive disorders, bulimia, anorexia, panic disorders, and premenstrual dysphoric disorders, mono amine oxidase inhibitors such as phenelzine for the palliative treatment of depression, and glucocorticoids for the treatment of inflammation of the nasal sinus cavity associated with chronic rhinosinusitis. The hydrogel compositions may be used as a carrier for synthetic and human-based bone regrowth agents such as recombinant human bone morphogenic protein as well as biomimetic materials usable for this indication such as B2A, F2A, PBA, LA1, VA5, PBA, LA1, VA5, B7A, F9A, FSA, and F20A from BioSurfaces Engineering Technology, heterodimeric chain synthetic heparin-binding growth factor analogs as taught in U.S. Pat. No. 7,528,105, positive modulator of bone morphogenic protein-2 as taught in U.S. Pat. Nos. 7,482,427 and 7,414,028, growth factor analogs as taught in U.S. Pat. No. 7,414,028, and synthetic heparin-binding growth factor analogs as taught in U.S. Pat. No. 7,166,574, all of which are incorporated herein by reference in their entirety.

The compositions of the current invention have a variety of uses especially in the area of cosmetic surgery and dermatology. Malleable, flowable compositions may be prepared as injectable formulations, and are suitable for superficial to deep dermal augmentation, for example to correct, fill, and support dermal wrinkles, creases, and folds as well as lips as taught in U.S. Pat. Nos. 5,827,937, 5,278,201 and 5,278,204. Larger volume injections can be envisioned for augmentation of breast, penile glans, and other anatomic positions in the body as taught in U.S. Pat. No. 6,418,934; all listed patents are incorporated herein by reference in their entirety.

Body sculpting procedures, including breast augmentation, are contemplated for cosmetic and reconstructive purposes. Augmentation of the glans of the penis is used for treatment of premature ejaculation. Historically, the main limitation of medical treatment for premature ejaculation is recurrence after withdrawal of medication. Glans penis augmentation using injectable compositions of the invention facilitate treatment of premature ejaculation via blocking accessibility of tactile stimuli to nerve receptors. The compositions of the invention could also be used as an injectable bulking agent for sphincter augmentation to control incontinence. In this application, the material is injected directly into the sphincter tissue to improve and augment the tissue structure such that sphincter control could be restored.

The composition described herein may be used as a space filling agent and energy barrier to attenuate existing energy-based procedures and reduce current dose limiting morbidity issues in adjacent tissue. The hydrogel composition of this invention acts as a transient buffer between the non-diseased tissue and the tumor target. The benefits of this approach are twofold; the space filling attribute of the formulation physically moves the collateral tissue away from the target tumor towards which the energy is applied, furthermore, the composition may be formulated to include additives that attenuate the strength of the applied radiation or other energy. For example, the composition may be used to mitigate or reduce radiation damage of the prostate during radiotherapeutic procedures. The displacement of the tumor away from healthy tissue described herein is also applicable to head and neck cancer, pelvic, thoracic, breast and soft tissue sarcomas. A further use of this composition in radiotherapy and surgical tumor removal procedures is using the composition as a marking system to delineate the boundary of the tumor.

The compositions of the current invention may be used to fill voids in tissue. Potential uses include the treatment of voids in bone, both weight bearing and non-weight bearing, the treatment of voids or gaps in articular cartilage, voids caused by a biopsy procedure, and septal defects of the heart. The treatment of these voids can be enhanced by the inclusion of biologically active agents and biologically activating agents in the hydrogel formulation. For example, recombinant human bone morphogenic protein or allograft human derived bone materials, or demineralized bone matrices, or synthetic biomimetic growth factor materials may be incorporated into the composition to aid in the treatment of bone voids.

The compositions described herein may be used to adhere two or more tissues to each other, or to adhere an implant or disposable medical device to a tissue. For example, a cured, partially hydrated variant of the formulation may be used to adhere a hearing aid to the ear drum. The ability of the semi-hydrated hydrogel to conduct pressure waves will allow the conduction of sound from the hearing aid to the middle ear. Further applications of the adhesive variants of the composition may include mucosal or buccal bandages or coverings for laceration of the dermis.

The compositions of the current environment can be may be used as a synthetic synovial fluid or other type of lubricating agent. By incorporating synthetic polymers that are highly hydrophilic, these materials may find application in fields such as tendon or ligament repair and thoracic surgery. The adhesion of a lacerated tendon that has undergone surgical repair to the tendon sheath reduces the range of motion of the affected digit or limb and increases the work required to attain the range of motion that remains. The deposition of a flowable slurry of the hydrogel composition between the surgically repaired tendon and the tendon sheath may act to reduce friction and enable a lower work of extension for the affected tendon. In another application, a thin layer of the composition may be sprayed onto or otherwise applied to a tendon to form a lubricous coating that prevents adhesion between the tendon and the tendon sheath. In thoracic surgery, adhesions may form after thoracic interventions. The introduction of a hydrogel described herein may prevent or reduce the formation of adhesions between the pleura, and in addition, provides a lubricant to movement of the adjacent tissue past each other.

The compositions described in the invention may be applied as a spray coating. The multiple components of the formulation may be applied sequentially or concurrently to enable curing via partial or full crosslinking at the target site. Spray coatings may be applied to a variety of medical devices and implants, including implantable orthopedic devices, coronary, peripheral, neurovascular stents, catheters, cannulas, and the like. Additionally, the spray coating may be applied to issues as a sealant or adhesion barrier, to wounds or lesions to aid in or accelerate healing or to act as a sealant, as a protective coating for the eye, or for drug delivery. As a detailed example, an orthopedic implant may be spray coated with formulations designed to promote osteogenesis and or osteoinduction and or osteoconduction, to prevent the formation of bacterial, microbial, or fungal colonies, to assist in the load bearing characteristics of the implant, or to act as a depot for the delivery of biologically active or biologically activating agents.

The compositions described in the invention may be applied as a liquid for in-situ curing via partial or complete crosslinking. The multiple components of the formulation may be applied sequentially or concurrently to enable curing or crosslinking at the target site. These embodiments may be applied by injecting the formulation into the core or recesses of implants to be placed in the body to provide local drug delivery including but not limited to analgesics, antibiotics, procoagulants, chemotherapeutic agents, and anticoagulants, or tissue engineering features including but not limited to osteogenesis, osteoinduction, and osteoconduction. Implants intended for placement in the body may also be dip coated in the liquid formulations described herein. These coatings may be allowed to dry for long term storage; they may be implanted in the dry or rehydrated state. In the dry form, it is anticipated that the material could be rehydrated in situ. The liquid formulations may be introduced into a tissue void including but not limited to bone voids, post biopsy orifices, and septal heart defects. The liquid formulations may be introduced to augment the shape or form of existing structures including but not limited to breast, lips, and naso-labial folds. The liquid formulations may also be used as an embolic for the treatment of but not limited to neurovascular and peripheral vascular aneurysms, uterine fibroids, metastatic and benign tumors, and varicose veins. The liquid formulation may be used to provide protection, lubrication, and cushioning to the eye following surgery. The liquid formulation may be used as a method for the delivery or application of drug, biologic, and biomimetic materials. The liquid formulation is also useful as sealant for the treatment of but not limited to access to the dura mater, access to the spine, or access to the vasculature.

The compositions described in this invention may be applied as a cured or substantially fully crosslinked material that may or may not be hydrated. Fields of use for this embodiment of the invention may include but are not limited to the following: wound healing as a preformed covering with or without an adhesive backing (as commonly used in bandage form), as a solid embolic for the treatment of neurovascular or peripheral aneurysms, uterine fibroids, metastatic and benign tumors, or varicose veins, as an adhesive to connect two or more tissues or materials, as an adhesive to attach implants such as a hearing aid to tissues, and as a method of drug delivery. The non-hydrated, cured (substantially fully crosslinked), materials may be subsequently processed (e.g. necking, stretching, forming, cutting, etc.) to attain other desirable characteristics. These processed materials may be used in the applications noted in the specification herein. For example, the hydrogel may be cast as a tube, and necked to a reduced diameter or profile that facilitates insertion into a tight lumen or limited space which is generally desirable in the art for minimally invasive and percutaneaous catheter based medical technologies. One specific example in which this embodiment would be useful is to control trauma wherein the cast hydrogel that has been necked would be inserted into narrow tissue wound formed by the passage of a bullet through said tissue. The material could be inserted by an emergency room technician in a civilian setting or a medic in a military setting as a fast acting tourniquet that facilitates movement of the patient to a more stable medical treatment environment. It is also contemplated as another example the treatment of neurovascular aneurysms wherein the non-hydrated, cured material would be necked to facilitate passage and delivery through the lumen of microcatheters commonly used in interventional neuroradiology procedures. The cured, necked hydrogel could then be deposited into the aneurysm similar to contemporary metallic detachable coils to facilitate closure or exclusion of the aneurysm.

The cured (fully or partially crosslinked) compositions described in this invention may be formulated as a powder. The powder is processed by being ground, milled, chopped, cryomilled, fragmented through syringe to syringe mixing, or any other process that may be used to reduce the size of a material to a desired particle size. The processes may be undertaken while the material is in the hydrated, partially hydrated, or non-hydrated forms. Alternatively, spray drying may be used to obtain a fine powder of the composition by employing hot gas to force a slurry of the composition out of an atomizer or spray nozzle. The slurry may contain the components of the composition in an unreacted, partially reacted, or fully reacted state. In some cases, the individual elements of the composition may be introduced to the atomizer or spray nozzle through separate feed lines to prevent the initiation of the crosslinking reaction prior to passage through the atomizer or spray nozzle. The partially crosslinked embodiment is particularly suited towards subsequent in situ or topical reactions where the reaction enables but is not limited to the following: acting as a sealant, acting as an embolic agent, acting as a hemostat, acting as a surface coating, acting as a lubricant, acting as an adhesive, acting as a void filler, acting as a space filling agent, or any of the other applications covered in this specification. This embodiment may have application as a topical dressing with hemostatic properties.

The compositions described in this invention may be formulated as a rehydrated powder. The rehydrated powder may consist of the cured (partially or fully crosslinked) hydrogel material that has been ground, milled, chopped, cryomilled, fragmented through syringe to syringe mixing, or any other process that may be used to reduce the size of a material to a desired particle size and subsequently rehydrated. This embodiment may have application in the following exemplary areas: the treatment of diabetic ulcers, the treatment of sinus and mucosal lesions, as an embolic agent, as a protective coating for tendon, ligament, or the pleural interface, as a method for drug delivery, as a method for tissue augmentation (dermal fillers, vocal fold filler, etc.), as a filler for breast implants, and as a filler for resorbable implants such as those used for placement against bone and for filling of voids such as between bones as taught in US. Published Pat. App. 2006/0241777 and herein incorporated by reference in their entirety.

Kits

Also provided are kits for use in practicing the subject methods, where the kits typically include the distinct substrate and crosslinker components of the composition, as described above. The substrate and crosslinker components may be present in separate containers in the kit, e.g., where the substrate is present in a first container and the crosslinker is present in a second container, where the containers may or may not be present in a combined configuration. The requisite buffer solutions for the substrate and crosslinker compositions may be provided in additional, separate, containers. Containers are understood to refer to any structure that may hold or surround the components of the hydrogel composition of the invention; exemplary containers include syringes, vials, pouches, capsules, carpules, ampules, cartridges, and the like. The containers may be shielded from visible, ultraviolet, or infrared radiation through the use of additional components (e.g. a foil pouch surrounding a syringe) or through selection of the material properties of the container itself (e.g. an amber glass vial or opaque syringe).

The subject kits may also include a mixing device, for mixing the substrates and crosslinking composition together to produce the composition of the invention. The kits may also include a delivery device (which may or may not include a mixing element), such as a catheter devices (e.g. tubes with one or more lumens of identical or differing sizes and shapes with exit points of varying geometries, dimensions, and positions), syringe(s) of similar or different diameters and volumes, spray elements, check valves, stopcocks, Y-connectors, air bleeder elements (e.g. a membrane that permits the removal of air from a liquid solution prior to delivery to the patient), inlet ports or chambers for the introduction of a forced air stream, disposable cartridges that allow for prolonged deposition of the hydrogel composition, applicators or spreaders, assemblies for realizing a mechanical advantage in delivering the composition of the invention, housings or casings to protect and contain the above mentioned components, and the like.

The kit may further include other components, e.g., desiccants or other means of maintaining control over water content in the kit, oxygen scrubbers or other means of maintaining control over oxygen content within the kit, an inert gas atmosphere (e.g. nitrogen or argon), indicators to convey the maximum temperature experienced by the kit, indicators to convey exposure to sterilizing radiation, ethylene oxide, autoclave conditions, and the like, retaining or positioning structures to prevent damage to the components (e.g. trays or packaging card), that are required to maintain the product in good condition during transport and storage.

Examples of a kit for the deployment and in situ formation of the hydrogel composition of the invention include, but are not limited to:

Two sealed vials, one containing the nucleophilic component(s) and the other containing the electrophilic component(s), two syringes, one containing the buffer for the nucleophilic component(s) and the other containing the buffer for the electrophilic component(s), a casing for containing and stabilizing the syringes, a casing for housing and stabilizing the vials, and a connecter element within the vial housing that holds needles positioned to pierce the septa on the vials when the syringe casing and vial casing are mated together. The user fills the syringes by mating the two casings (driving the needles through the respective septa), injecting the buffer solutions into the vials, and withdrawing the reconstituted solutions into the syringes. The user may then attach a delivery device to the syringes as needed (see exemplary delivery device elements above for a non-inclusive list).

A second kit for in situ delivery and formation of the hydrogel formulation may consist of two dual chamber mixing syringes (e.g. Vetter Lyo-Ject®); one syringe contains the nucleophilic powder and the nucleophilic buffer, the other contains the electrophilic powder and electrophilic buffer, and a syringe casing that houses the two dual chamber syringes. The user depresses the syringe plungers to transfer the buffers from the proximal chambers into the distal powder chambers and reconstitute the powders. The user may then attach a delivery device to the syringes as needed (see exemplary delivery device elements above for a non-inclusive list).

A third kit for in situ delivery and formation of the hydrogel formulation may consist of a syringe containing the nucleophilic substrate reconstituted with an appropriate buffer, a sealed vial containing the electrophilic substrate powder, a second syringe containing the electrophilic buffer, a casing for containing and stabilizing the syringes, a casing for housing and stabilizing the single vial, and a connecter element within the vial housing that holds a needle positioned to pierce the septum on the vial when the syringe casing and vial casing are mated together. The user fills the syringes by mating the two casings (driving the needle through the septum), injecting the electrophilic buffer solution into the vial, and withdrawing the reconstituted solution into the syringe. The user may then attach a delivery device to the syringes as needed (see exemplary delivery device elements above for a non-inclusive list).

A fourth kit for in situ delivery and formation of the hydrogel formulation may consist of a syringe containing the nucleophilic substrate reconstituted with an appropriate buffer and a sealed chamber containing the freeze dried electrophilic powder separated by a one way check valve. Depressing the syringe introduces the nucleophile solution into the electrophile powder chamber, rapidly reconstituting the electrophile and beginning the crosslinking reaction. Continued depression of the syringe pushes the activated solution out of the powder chamber and into the accessory components (e.g. a mixing element, cannula or spray tip, etc. as listed above).

A fifth kit for in situ delivery and formation of the hydrogel formulation may consist of two syringes, one containing the nucleophilic substrate reconstituted with an appropriate buffer and the other containing the electrophilic substrate reconstituted with an appropriate buffer, and a syringe casing. The user may then attach a delivery device to the syringes as needed (see exemplary delivery device elements above for a non-inclusive list).

A sixth kit for the in situ delivery and formation of the hydrogel formulation may consist of a sponge or swab containing a dry form of the polysaccharide substrate, physiologically acceptable polymer substrate, crosslinking composition, and appropriate buffer salts. The user can deposit a layer of the cured hydrogel formulation by wetting the swab with saline and wiping the wet swab across the target tissue or area. The saline reconstitutes the four components within the swab and begins the crosslinking reaction; this reaction completes after the activated components have been deposited at the target, resulting in the formation of the crosslinked hydrogel formulation. Alternatively, the reaction may be driven by contacting the swab containing the four components with a moist tissue surface such as the cornea of the eye.

Other kits may be envisioned for the use of a hydrogel formulation that has been cured prior to shipment to the user. The following examples are non-limiting and are meant to demonstrate the potential for kitting the hydrogel formulation.

In one embodiment, a container provides the cured, dried, and fragmented hydrogel formulation. A syringe is supplied containing a buffer appropriate for rehydrating the powder. The syringe is connected to the fragmented hydrogel container and the buffer is introduced to the container to rehydrate the fragmented hydrogel. The rehydrated hydrogel formulation is withdrawn into the syringe, at which point the user can connect it to any of the exemplary device elements previously listed.

In a second embodiment, both the cured, dried, and fragmented hydrogel formulation and the appropriate buffer solution are provided in a dual chamber syringe. The user rehydrates the dry hydrogel fragments by depressing the syringe plunger and combining the buffer solution with the dry hydrogel fragments. The user can then connect the syringe to any of the exemplary device elements previously listed.

In a third embodiment, the cured, dried and fragmented hydrogel formulation is provided in a syringe in the rehydrated state. The user can connect the syringe to any of the exemplary device elements that have been previously listed.

In fourth embodiment, the cured, dried and fragmented hydrogel formulation is provided in a pouch or container for direct application to the target site.

In a fifth embodiment, the cured hydrogel may be dried and provided in any form or geometry. For example, the cured hydrogel may be provided as a thin cylinder for insertion through a catheter; the same form of hydrogel may be provided loaded into a catheter or into a cartridge intended for insertion into a neurovascular catheter. Alternatively, the cured hydrogel may be provided as a spiral or conical spiral for insertion into the nasal cavity to prevent nasal valve collapse and maintain airway patency. In another example, the cured hydrogel may be provided as a woven stent for prevention of tracheal or nasal passage collapse, or for the prevention of adhesion formation between the inner surfaces of a body lumen as taught in U.S. Pat. No. 6,322,590, incorporated herein by reference in its entirety. In yet another example, the cured hydrogel may be provided as a sheet for use as a bandage or dressing. As yet another example, a freeze dried hydrogel formulation may be attached to an adhesive film for use as a bandage or dressing. In an additional example, the hydrogel may be coated on a coiled wire and dried for insertion into a neurovascular aneurysm. When exposed to blood within the aneurysm, the hydrogel coating swells and takes up a much larger space than the coil itself or the combination of the coil and dry hydrogel.

In a sixth embodiment, the cured hydrogel may be dried and rehydrated and provided in any form or geometry. For example, the rehydrated hydrogel may be provided in a sheet for use as a moist wound covering. In another example, the rehydrated hydrogel may be attached to an adhesive film as a dressing or moist wound covering.

In a seventh embodiment, the cured hydrogel may be provided in a kit with a saline rinse that is pH balanced to accelerate the degradation of the hydrogel. For example, a freeze-dried hydrogel may be provided as a sheet for use in adhesion prevention in which the application of the saline rinse results in a faster degradation of the sheet with respect to the degradation rate of the freeze-dried hydrogel absent the rinse.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 4:
FIG. 4 shows an exemplary composition of a PEG-PEG-Chitosan hydrogel.

A multi-armed polyethylene glycol with amine active groups was combined with chitosan at a 10:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution. After one hour had passed, a firm, clear hydrogel had formed (FIG. 4).

Example 2

Three samples were sectioned from a hydrogel fabricated as described in Example 1, weighed, and placed in phosphate buffered saline at 37 C. After twenty four hours had passed, the samples were weighed and the amount of swelling over that time period was calculated as: $100*(m24-m0)/m0$, where m0 is the mass of the sample at time zero and m24 is the mass of the sample at twenty four hours. The hydrogels had swelled an average of 143% during over a period of twenty four hours.

Example 3

Figure 5:
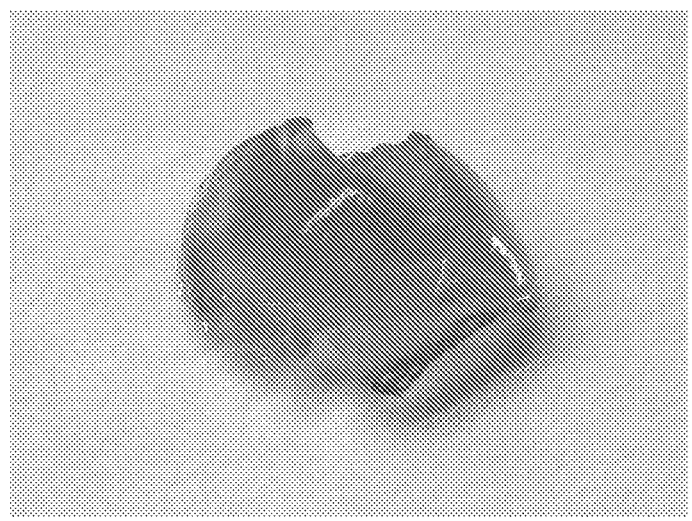
FIG. 5 shows an exemplary composition of a PEG-GA-Chitosan hydrogel.

A multi-armed polyethylene glycol with amine active groups was combined with chitosan at a 10:1 ratio of polyethylene glycol to chitosan in sodium borate buffer. An equal volume of sodium phosphate buffer containing 4% glutaraldehyde (GA) was combined with the chitosan solution. After one hour had passed, a firm, yellow-brown gel had formed (FIG. 5).

Example 4

Figure 6:
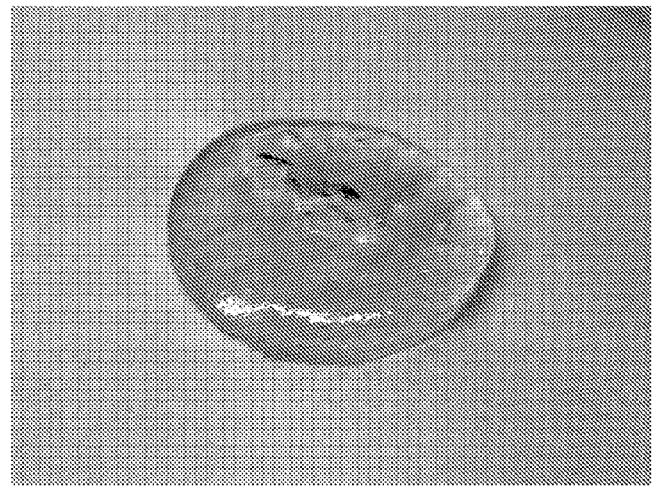
FIG. 6 shows an exemplary composition of a PEG-PEG-carboxymethylcellulose hydrogel.

A multi-armed polyethylene glycol with amine active groups was combined with carboxymethylcellulose (CMC) at a 4:1 ratio of polyethylene glycol to carboxymethylcellulose in sodium borate buffer. An equal volume of a multi-armed polyethylene glycol with ester active groups reconstituted in sodium borate buffer at a 1:1 ratio of polyethylene glycol ester to polyethylene glycol amine was mixed with the carboxymethylcellulose solution. After one hour had passed, a soft, clear hydrogel had formed (FIG. 6).

Example 5

Figure 7:
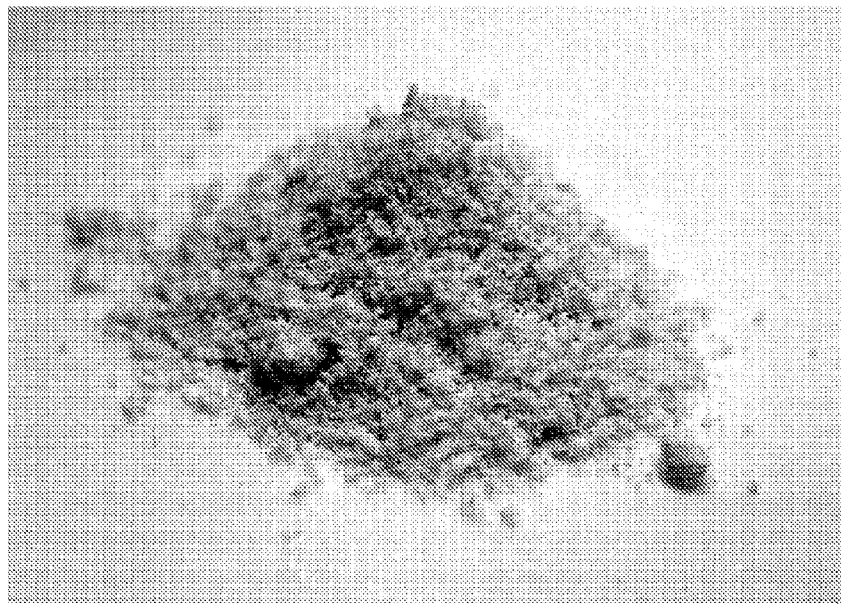
FIG. 7 shows an exemplary composition of a PEG-PEG-chitosan hydrogel cryomilled into a particulate form.

A multi-armed polyethylene glycol with amine active groups was combined with chitosan at a 5:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution. After one hour had passed, a firm, clear hydrogel had formed. The hydrogel was dried to a constant mass and ground into particulate with a cryogrinding process. An image of the cryomilled particulate is shown in FIG. 7.

Example 6

Figure 8:
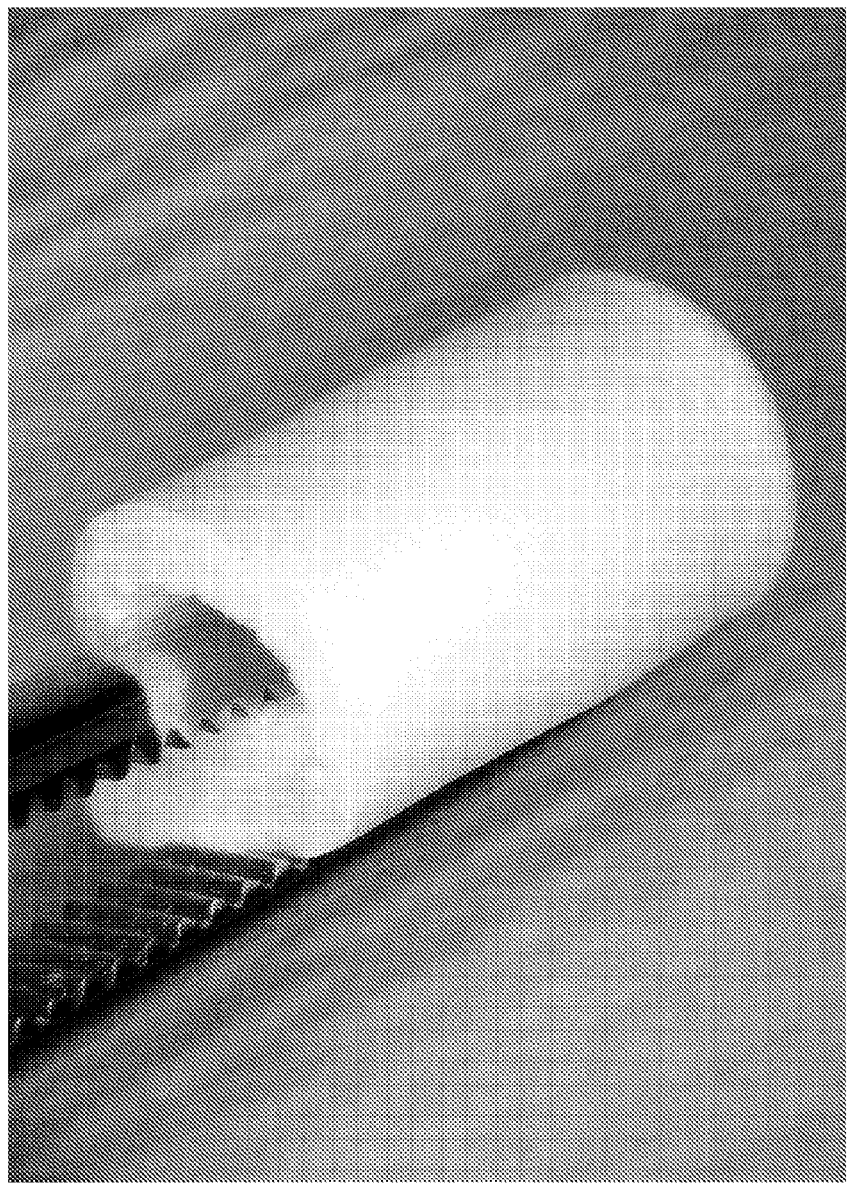
FIG. 8 shows an exemplary composition of a freeze-dried PEG-PEG-chitosan hydrogel rolled into a tube and held by a pair of forceps.

A multi-armed polyethylene glycol with amine active groups was combined with chitosan at a 5:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution, and the combined solutions were cast into a tray to a depth of approximately 3 mm. The sample was subjected to freeze-drying, after which a 1 cm by 1 cm sample was cut from the larger sample. The material had the consistency of a sponge or dense gauze; it could be manipulated with operations like rolling, pressing, and folding without noticeable damage or tearing. FIG. 8 shows the sample material rolled on itself and held in a pair of forceps.

Example 7

Figure 9:
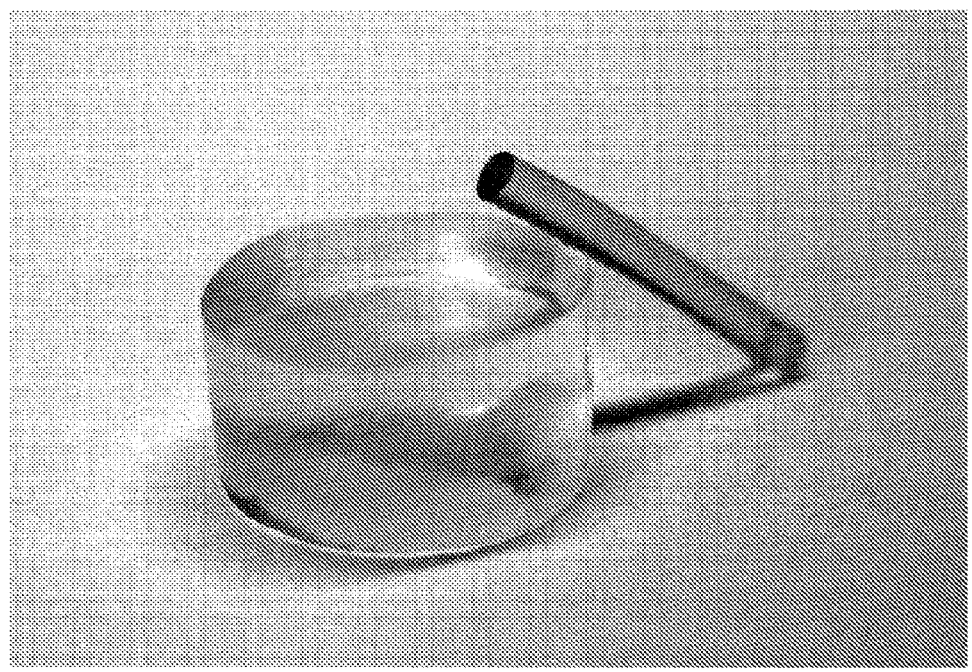
FIG. 9. shows an exemplary composition of a shape-memory embodiment of a PEG-PEG-chitosan hydrogel in the dry and hydrated states.

A multi-armed polyethylene glycol with amine active groups was combined with chitosan at a 15:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution, and the combined solutions were cast into a cylindrical mold 0.25" in diameter. The composition was allowed to cure, then it was removed from the mold and air dried to a constant mass and outer diameter of 0.114". The diameter of the rod was further reduced to 0.033" from its cast dimension via a necking process. A sample of the necked rod was cut to a length of 0.5" and placed in water; the mass, length, and diameter of the sample was tracked over time. At approximately 24 hours of exposure to water, the sample had exhibited a 1285% increase in mass, a 44% decrease in length, and a 481% increase in diameter. FIG. 9 shows a sample of the material in the dry and hydrated states.

Example 8

Figure 10:
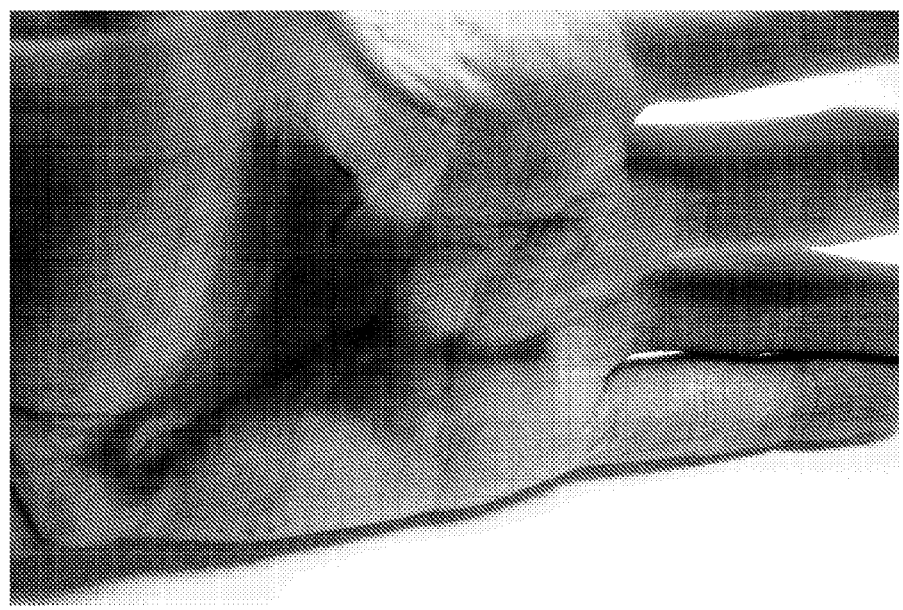
FIG. 10 shows an exemplary composition of a PEG-PEG-chitosan hydrogel applied as a spray in a thin coating to a human palm.

A multi-armed polyethylene glycol with amine active groups was combined with chitosan at a 5:1 ratio of polyethylene glycol to chitosan in sodium borate buffer with methylene blue as a colorant. This solution was loaded into a 1 milliliter syringe. An equal volume of a multi-armed polyethylene glycol with ester active groups reconstituted in sodium phosphate buffer at a 2:1 ratio of polyethylene glycol ester to polyethylene glycol amine was loaded into a second 1 mm syringe. The syringes were joined to a syringe handle, overmolded connector, mixing element, and spray tip. The delivery system was used to apply a thin, conformable coating of the hydrogel composition to a human hand that cured within seconds of application. The coating was able to adhere to the skin when held in a vertical orientation and could withstand flexure of the palm without rupture or cracking (FIG. 10).

Example 9

A multi-armed polyethylene glycol with amine active groups was combined with chitosan at a 9:1 ratio of polyethylene glycol to chitosan in sodium borate buffer. This solution was loaded into one of the two barrels on a dual syringe applicator. An equal volume of a multi-armed polyethylene glycol with ester active groups was reconstituted in sodium phosphate buffer at a 2:1 ratio of polyethylene glycol ester to polyethylene glycol amine. Methylene blue was added to the sodium phosphate solution for visualization purposes and the solution was loaded into the second barrel of the dual syringe applicator. The dual syringe applicator was combined with plunger caps, a dual syringe plunger, and a spray tip.

Figure 11:
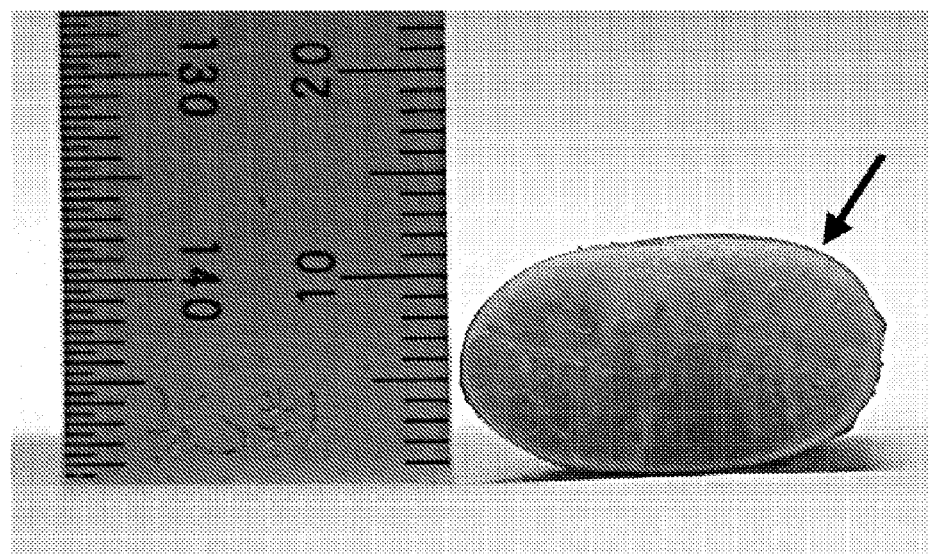
FIG. 11 shows a cross-sectional view of a bovine tendon coated with an exemplary composition of a PEG-PEG-chitosan hydrogel.

A section of explanted bovine tendon and an intacted section of the tendon sheath was cut to approximately 3 inches in length. The tendon was advanced out of the sheath until approximately 1.5 inches of the tendon was exposed. The delivery system was used to apply a thin (sub-millimeter), conformable coating of the hydrogel composition to the outer surface of the tendon. After four seconds, the tendon was retracted into the sheath using a pair of forceps. The coating was lubricious and non-friable, remaining intact and adherent to the tendon over the course of 20 extension/retraction cycles. FIG. 11 shows a cross sectional image of the bovine tendon with the coating identified by an arrow.

Example 10

Figure 12:
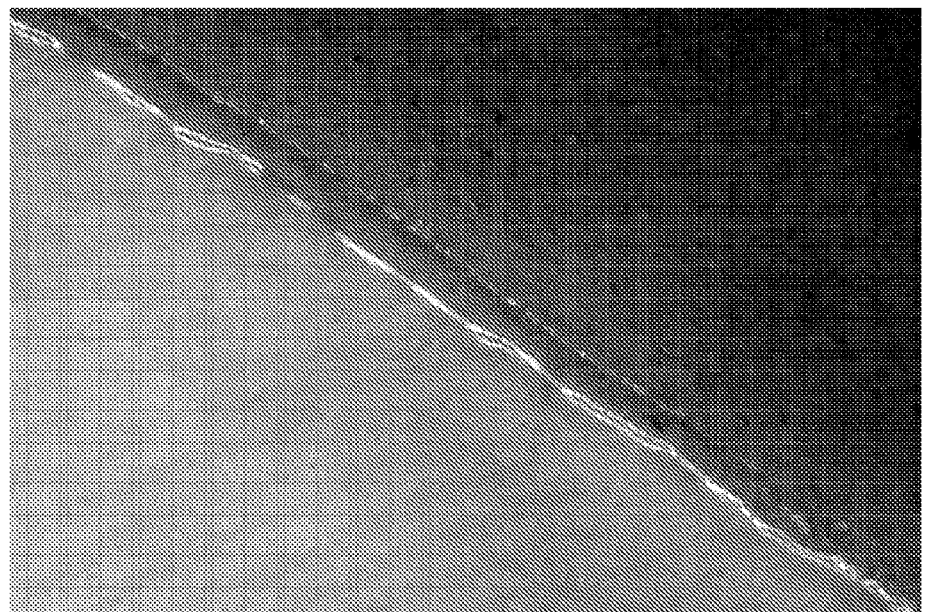
FIG. 12 shows a perspective view of a spray coating of an exemplary composition of a PEG-glutaraldehyde-chitosan hydrogel applied to a human hand.

A multi-armed polyethylene glycol with amine active groups was combined with chitosan at a 17:1 ratio of polyethylene glycol to chitosan in sodium borate buffer. This solution was loaded into one of the two barrels on a dual syringe applicator. An equal volume of heat treated glutaraldehyde and dextran was reconstituted in sterile water for injection at a heat treated glutaraldehyde:polyethylene glycol ratio of 1:42.5 and a dextran:polyethylene glycol ratio of 1:10 polyethylene glycol. The heat treated glutaraldehyde/dextran solution was loaded into the second barrel of the dual syringe applicator. The dual syringe applicator was combined with plunger caps, a dual syringe plunger, and a spray tip. The delivery system was used to apply a thin, conformable coating of the hydrogel composition to a human hand. The coating was able to adhere to the skin when held in a vertical orientation and could withstand flexure of the palm without rupture or cracking. FIG. 12 shows a perspective view of the coating as adhered to the skin.

Example 11

A multi-armed polyethylene glycol with amine active groups was combined with chitosan at a 9:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution, and the combined solutions were cast into a tray to a depth of approximately 3 mm. The sample was subjected to freeze-drying, after which a 1 cm by 1 cm sample was cut from the larger sample. The sample was placed in a solution of sterile saline to swell for 1 hour.

Concurrently, a kit for the application of a spray coating of the composition was prepared by fabricating a solution of a multi-armed polyethylene glycol with amine active groups was combined with chitosan at a 22:1 ratio of polyethylene glycol to chitosan in an alkaline solution of FD&C Blue No. 1 in sodium borate buffer. This solution was loaded into one of the two barrels on a dual syringe applicator. An equal volume of a multi-armed polyethylene glycol with ester active groups was reconstituted in sodium phosphate buffer at a 2:1 ratio of polyethylene glycol ester to polyethylene glycol amine. The dual syringe applicator was combined with plunger caps, a dual syringe plunger, and a spray tip.

Figure 13:
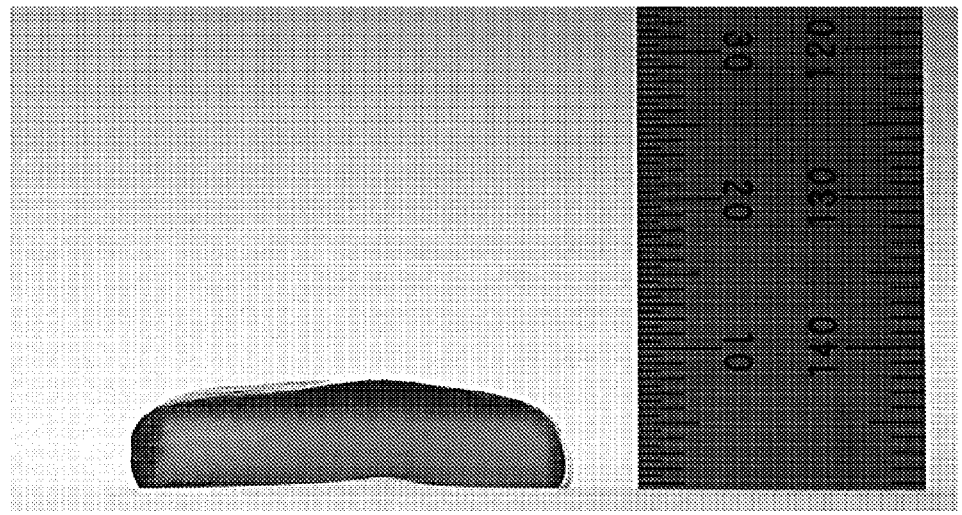
FIG. 13 shows a cross-sectional view of an exemplary composition of a freeze-dried PEG-PEG-chitosan hydrogel coated with an exemplary composition of a PEG-PEG-chitosan hydrogel.
Figure 14:
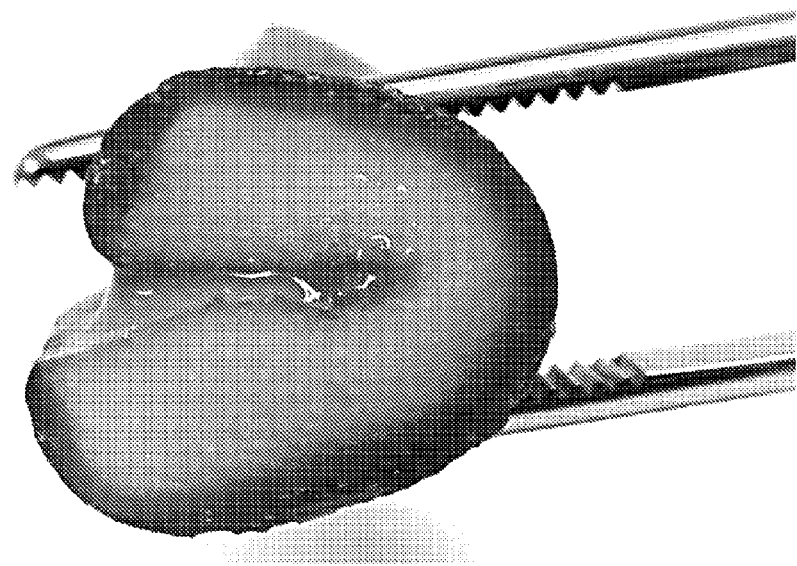
FIG. 14 shows a cross-sectional view of an exemplary composition of a freeze-dried PEG-PEG-chitosan hydrogel coated with an exemplary composition of a PEG-PEG-chitosan hydrogel doubled on itself and held in a pair of forceps.

The rehydrated hydrogel was removed from the sterile saline and the dual syringe applicator was used to apply a coating of the in-situ crosslinking form of the composition onto the surface of the hydrogel. FIG. 13. shows a cross section of the coated hydrogel with a ruler as a reference; the scale on the ruler is in millimeters. The coating appeared to adhere and integrate into the surface of the hydrogel, and did not delaminate or fracture when flexed or bent. FIG. 14. shows a cross section of the coated hydrogel held by forceps in a double-over configuration. The coated hydrogel was returned to the sterile saline for 24 hours. At the end of this time, the hydrogel coating had swelled to a degree notable via visual inspection, however, the coating had not fractured, delaminated, or developed any fissures or irregularities.

Example 12

Figure 15:
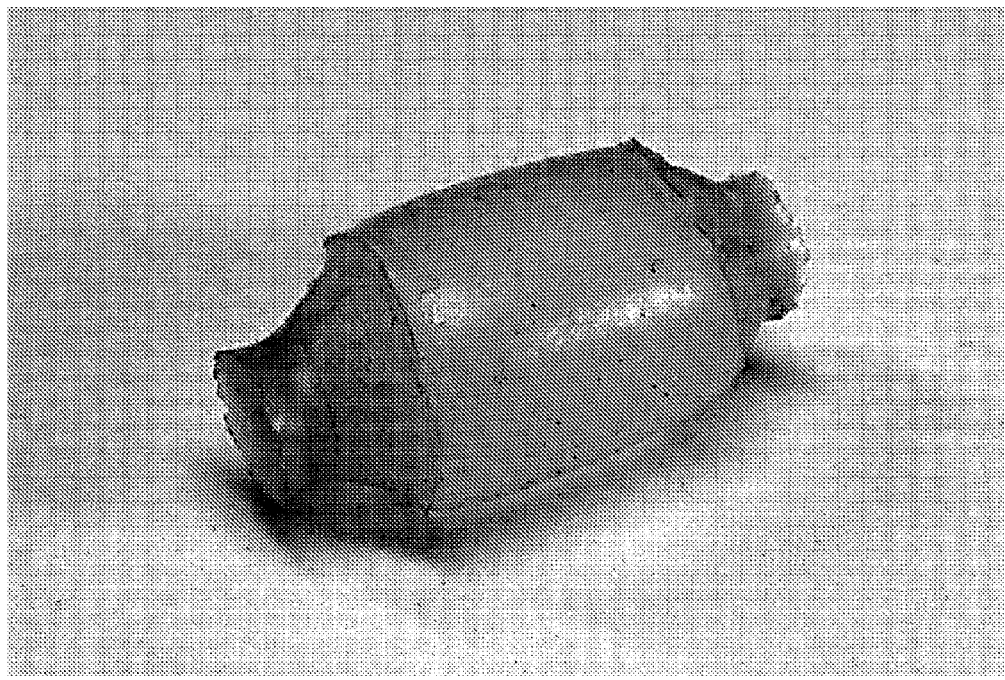
FIG. 15 shows a hollow chamber formed from an exemplary composition of a PEG-PEG-chitosan hydrogel.

A multi-armed polyethylene glycol with amine active groups was combined with chitosan at a 9:1 ratio of polyethylene glycol to chitosan in sodium borate buffer. An equal volume of a multi-armed polyethylene glycol with ester active groups reconstituted in sodium borate buffer at a 2:1 ratio of polyethylene glycol ester to polyethylene glycol amine was mixed with the chitosan solution, and the combined solutions were cast into a cylindrical mold. The volume of the combined solution was less than that of the mold. The mold was fixed in a lathe and spun to coat the internal walls of the mold with the solution. When the hydrogel had cured, the mold was removed from the lathe and opened to allow the hydrogel to dry and form a hollow, balloon like structure. FIG. 15. shows the hydrogel structure at end of the drying period.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A hydrogel composition, comprising
carboxymethylchitosan having a molecular weight of less than or equal to 5,000 Dalton, a degree of deacetylation of 70% to 99%, an electrophilic group, and at least two nucleophilic groups, wherein carboxymethylchitosan is soluble in an aqueous solution;
a multifunctional, multi-armed polyethylene glycol polymer of a molecular weight of 5,000 Dalton to 30,000 Dalton, and comprising at least two nucleophilic groups; and
a multifunctional, multi-armed crosslinker of polyethylene glycol having a molecular weight of 5,000 Dalton to 30,000 Dalton, and comprising at least two electrophilic groups;
wherein the multifunctional, multi-armed polyethylene glycol polymer comprises ester groups to provide for degradation via hydrolysis and
wherein the hydrogel composition comprises:
a covalent bond between carboxymethylchitosan and the multifunctional multi-armed polyethylene glycol polymer;
a covalent bond between carboxymethylchitosan and the multifunctional multi-armed crosslinker and
a covalent bond between the multifunctional multi-armed polyethylene glycol polymer and the multifunctional multi-armed crosslinker.

2. The composition of claim 1, wherein carboxymethylchitosan is present in the composition from 0.5% to 10% by mass.

3. The composition of claim 1, further comprising one or more of a thickening agent, filler, a foaming agent, a biologically active agent, a pharmaceutically active agent, a visualization agent, or a radiopaque agent.

4. The composition of claim 3, wherein the composition comprises a biologically active agent.

5. The composition of claim 4, wherein the biologically active agent is a plasma protein, hormone, enzyme, antiseptic agent, antibiotic, antineoplastic agent, antifungal agent, antiviral agent, anti-inflammatory agent, human or non-human growth factor, anesthetic, cell suspension, cytotoxins, cell proliferation inhibitors, fibrin, fibrinogen, collagen or biomimetic.

6. The composition of claim 3, wherein the composition comprises a filler selected from the group consisting of hydroxyapatite, fibrous silk, carbon fiber, bone chips and a mesh of polyglycolic acid.

7. The composition of claim 3, wherein the composition comprises a visualization agent.

8. The composition of claim 3, wherein the composition comprises a radiopaque agent.

9. A hydrogel composition, comprising:
  dicarboxyl chitosan having a molecular weight of less than or equal to 5,000 Dalton, a degree of deacetylation of 70% to 99%, an electrophilic group, and at least two nucleophilic groups, wherein the dicarboxyl chitosan is soluble in an aqueous solution;
  a multifunctional, multi-armed polyethylene glycol polymer of a molecular weight of 5,000 Dalton to 30,000 Dalton, and comprising at least two nucleophilic groups; and
  a multifunctional, multi-armed crosslinker of polyethylene glycol having a molecular weight of 5,000 Dalton to 30,000 Dalton, and comprising at least two electrophilic groups;
  wherein the multifunctional, multi-armed polyethylene glycol polymer comprises ester groups to provide for degradation via hydrolysis and
  wherein the hydrogel composition comprises:
    a covalent bond between dicarboxyl chitosan and the multifunctional multi-armed polyethylene glycol polymer;
    a covalent bond between dicarboxyl chitosan and the multifunctional multi-armed crosslinker and
    a covalent bond between the multifunctional multi-armed polyethylene glycol polymer and the multifunctional multi-armed crosslinker.

10. The composition of claim 9, wherein dicarboxyl chitosan is present in the composition from 0.5% to 10% by mass.

11. The composition of claim 9, further comprising one or more of a thickening agent, filler, a foaming agent, a biologically active agent, a pharmaceutically active agent, a visualization agent, or a radiopaque agent.

12. The composition of claim 11, wherein the composition comprises a biologically active agent.

13. The composition of claim 12, wherein the biologically active agent is a plasma protein, hormone, enzyme, antiseptic agent, antibiotic, antineoplastic agent, antifungal agent, antiviral agent, anti-inflammatory agent, human or non-human growth factor, anesthetic, cell suspension, cytotoxins, cell proliferation inhibitors, fibrin, fibrinogen, collagen or biomimetic.

14. The composition of claim 11, wherein the composition comprises a filler selected from the group consisting of hydroxyapatite, fibrous silk, carbon fiber, bone chips and a mesh of polyglycolic acid.

15. The composition of claim 11, wherein the composition comprises a visualization agent.

16. The composition of claim 11, wherein the composition comprises a radiopaque agent.

* * * * *